US006906105B2

(12) United States Patent
Bowen et al.

(10) Patent No.: US 6,906,105 B2
(45) Date of Patent: Jun. 14, 2005

(54) CHALCONE AND ITS ANALOGS AS AGENTS FOR THE INHIBITION OF ANGIOGENESIS AND RELATED DISEASE STATES

(76) Inventors: J. Phillip Bowen, 129 Hidden Lake, P.O. Box 250, Hull, GA (US) 30646; Thomas Philip Robinson, 512 Beaver Dam Run, Durham, NC (US) 27703-8008; Tedman Ehlers, 100 Stone Mill Run #9, Athens, GA (US) 30605; David Goldsmith, 337 Chelsea Cir., Atlanta, GA (US) 30307; Jack Arbiser, 1690 Parliament Point, Atlanta, GA (US) 30329

( * ) Notice: Subject to any disclaimer, the term of this patent is extended or adjusted under 35 U.S.C. 154(b) by 0 days.

(21) Appl. No.: 10/198,786

(22) Filed: Jul. 18, 2002

(65) Prior Publication Data

US 2003/0027830 A1 Feb. 6, 2003

Related U.S. Application Data

(62) Division of application No. 09/748,599, filed on Dec. 26, 2000, now Pat. No. 6,462,075.
(60) Provisional application No. 60/171,883, filed on Dec. 23, 1999.

(51) Int. Cl.$^7$ .......................... A61K 31/12; C07C 49/213
(52) U.S. Cl. ........................................ 514/679; 568/325
(58) Field of Search .................................. 514/679, 629; 568/325

(56) References Cited

U.S. PATENT DOCUMENTS

| 5,414,015 A | 5/1995 | Konoshima et al. |
| 5,703,130 A | 12/1997 | Han et al. |
| 5,716,982 A | 2/1998 | Han et al. |
| 5,773,646 A | 6/1998 | Chandrakumar et al. |
| 5,877,207 A | 3/1999 | Klein et al. |
| 6,462,075 B1 | 10/2002 | Bowen et al. |

FOREIGN PATENT DOCUMENTS

| EP | 0 998 939 | 5/2000 |
| WO | WO 96/30004 | 10/1986 |
| WO | WO 99/00114 A | 1/1999 |

OTHER PUBLICATIONS

Levai et al, Indian Journal of Chemistry, vol. 35B, No. 10, pp. 1091–1096, 1996.*
Safak et al, Journal of Indian Chem Society, vol. 67, No. 7, pp. 571–574, 1990.*
Nakamura et al. "Interaction of Myofibroblast and Endothelial Cell in Healing Process of Ethanol–Induced Gastric Mucosa", *World Congr. Microcir. 6$^{th}$*, (abstract), 1996.
Kobayashi et al. "Inhibitory Effect of Isoliquiritin, a Compound in Licorice Root, on Angiogenesis in Vivo and Tube Formation in Vitro", *Biol. Pharm. Bull.*, 18(11): pp. 1382–1286 (abstract), 1995.

Oikawa et al., "A highly Potent Antiangiogenic Activity of Retinoids", *Cancer Lett.*, 48(2): pp. 157–162 (abstact), 1989.
Murakami et al. "Cancer Chempreventive Potentials of Edible Thai Plants and Some of Their Active Constituents", *Mem. Sch. Bio.–Oriented Sci. Technol. Kinki Univ.*, 1: pp. 1–23 (abstract), 1997.
Chen et al. "Inhibition of Farnesyl Protein Transferase, H–Ras Oncogene Expression and P21ras Membrane Association by Natural Products in Human Solid Tumor Cell Lines", *J. Asian Nat. Prod. Res.*, 1(1): pp. 29–51 (abstract), 1998.
Bois et al., "Halogenated Chalcones with High–Affinity Binding to P–Glycoprotein: Potential Modulators of Multi-drug Resistance", *J. Med. Chem.*, 41(21): pp. 4161–4164 (abstract), 1998.
Aono et al., "Preparation of Fused Ring Compounds as Drugs", PCT Int'l Appln. (WO 98/37070), Abstract. 1998.
Lee et al., "Evaluation of the Antioxidant Potential of Natural Products", *Comb. Chem. High Throughput Screening*, 1(1): pp. 35–46 (abstract), 1998.
White et al., "Screening of Potential Cancer Preventing Chemicals for Induction of Glutathione in Rat Liver Cells", *Oncol. Rep.*, 5(2): pp. 507–512 (abstract), 1998.
Chang et al. "Effect of Ginseng Extracts on Production of Vacuolating Toxin By Helicobacter Pylori", *Taehan Misaengmul Halhoechi*, 32(5): abstract, 1997.
Sun et al. "Differential Effects of Synthetic Nuclear Retinoid Receptor–Selective Retinoids on the Growth of Human Non–Small Cell Lung Carcinoma Cells", *Cancer Res.*, 57(12): pp. 4931–4939 (abstract), 1997.
Zhang et al. "Glutathione Conjugation of Chlorambucil: Measurement and Modulation by Plant Polyphenols", *Biochem. J.*, 325(2): pp. 417–422 (abstract), 1997.
Markaverich et al., "Methyl P–Hydroxyphenyllactate, Its Analogs and Derivatives, as Neoplasm Inhibitors", PCT Int'l Appln (WO 89/00849), abstract, 1989.
Glinkowska et al. "The Effect of Phenolic Compounds of Poplar Leaves Extract on Cutaneous Angiogeneis Reaction", *Acta Pol. Pharm.*, 54(2): pp. 151–154 (abstract), 1997.

(Continued)

*Primary Examiner*—Zinna Northington Davis
(74) *Attorney, Agent, or Firm*—Henry D. Coleman; R. Neil Sudol; William J. Sapone

(57) ABSTRACT

The present invention relates to chalcone and chalcone derivatives and analogs which are useful as angiogenesis inhibitors. The present compounds, which are inexpensive to synthesize, exhibit unexpectedly good activity as angiogenesis inhibitors. The present invention also relates to the use of chalcone and its analogs as antitumor/anticancer agents and to treat a number of conditions or disease states in which angiogenesis is a factor, including angiongenic skin diseases such as psoriasis, acne, rosacea, warts, eczema, hemangiomas, lymphangiogenesis, among numerous others, as well as chronic inflammatory disease such as arthritis.

10 Claims, 14 Drawing Sheets

OTHER PUBLICATIONS

Domange et al. "Pharmacological Studies of Cyclo–3–Fort and Its Constituents (Ruscus Extract, Hesperidin Methyl Chalcone, Ascorbic Acid)", *Clincal Hemorheology*, 14(1):Abstract, 1994.

Devincenzo et al., "In Vitro Evaluation of Newly Developed Chalcone Analogues in Human Cancer Cells", *Cancer Chemotherapy and Pharmacology*, 46(4): pp. 305–312 (Abstract), 2000.

Rafi et al., "Modulation of BCl–2 and Cytotoxicity by Licochalcone–A, a Novel Estrogenic Flavonoid", *Anticancer Research*, 20(4): pp. 2653–2658 (Abstract), 2000.

Han, R. "Research and Development of Cancer Chemopreventive Agents in China", *Journal of Cellular Biochemistry*, 27: pp. 7–11 (Abstract), 1997.

Makita et al. "Chemoprevention of 4–Nitraquinoline 1–Oxide–Induced Rat Oral Carcinogenesis by the Dietary Flavonoids Chalcone, 2–Hydroxychalcone, and Quercetin", *Cancer Research*, 569210: pp. 4904–4909 (Abstract), 1996.

Cluzan et al., "Treatment of Secondary Lymphedema of the Upper–Limb with Cyclo–3–Fort", *Lymphology*, 29(1): ppl 29–35 (Abstract), 1996.

Devincenzo et al. "Effect of Synthetic and Naturally–Occurring Chalcones on Ovarian Cancer Cell–Growth Structure–Activity Relationships", *Anti–cancer Drug Design*, 10(6): pp. 481–490 (Abstract), 1995.

Wattenberg, L. "Chalcones, Myoinositol and Other Novel Inhibitors of Pulmonary Carcinogenesis", *Journal of Celloular Biochemistry*, 22: pp. 162–168 (Abstract), 1995.

Yit, C. C. and Das, N. P. "Cytotoxic Effect of Butein on Human Colon Adenocarinoma Cell–Proliferation", *Cancer Letters*, 82(1): pp. 65–72 (Abstract), 1994.

Wattenberg et al. "Inhibition of Carcinogen–Induced Pulmonary and Mammary Carcinogenesis by Chalcone Administered Subsequent to Carcinogen Exposure", *Cancer Letters*, 83(1–2): pp. 165–169 (Abstract), 1994.

Ramanathan et al. "Inhibition of Tumor Promotion and Cell–Proliferation by Plant Polyhenols", *Phytotherapy Research*, 8(5): pp. 293–296 (Abstract), 1994.

Shibata, S. "Anti–Tumorigenic Chalcones", *Stem Cells*, 12(1): pp. 44–52 (Abstract), 1994.

Satomi, Y. "Inhibitory Effects of 3'–Methyl–Hydroxy–Chalcone on Proliferation of Human–Malignant Tumor–Cells and on Skin Carcinogenesis", *International Journal of Cancer*, 55(3): pp. 506–514 (Abstract), 1993.

Ramanathan et al. "Inhibitory Effects of 2–Hydroxy Chalcone and other Flavonoids on Human Cancer Cell–Proliferation", *International Journal of Oncology*, 3(1): pp.115–119 (Abstract), 1993.

Shibata, S. "A Drug Over the Millennia: Pharmacognosy, Chemistry, and Pharmacology of Licorice", *Yakugaku Zasshi–Journal of the Pharmaceutical Society of Japan*, 120(10): pp. 849–862 (Abstract), 2000.

Herencia et al. "Novel Anti–Inflammatory Chalcone Derivatives Inhibit the Induction of Nitric Oxide Synthase and Cyclooxygenase–2 in Mouse Peritoneal Macrophages", *FEBS Letters*, 453(1–2): pp. 129–13 4 (Abstract), 1999.

Sheahan et al. "The colorless Flavonoids of arabidopsis Thaliana (Brassicaceae). I. A Model System to Study the Orthodihydroxy Structure", *American Journal of Botany*, 85(4): pp. 467–475 (Abstract), 1998.

Iwata et al. "Antitumorigenic Activities of Chalcones—(II). Photo–Isomerization of Chalcones and the Correlation with Their Biological Activities", *Biological & Pharmaceutical Bulletin*, 20(12) pp. 1266–1270 (Abstract), 1997.

Chang et al. "Activity–Guided Isolation of Constituents of Tephrosia–Purpurea with the Potential to Induce the Phase–II Enzyme, Quinone Reductase", *Journal of Natural Products*, 60(9): pp. 869–873 (Abstract), 1997.

Miyamoto, T. and Yamamoto, I. "Inhibition of Housefly Glutathione–S–Transferase by Chalcone and Comparison of Its Isozymes with Rat", *Journal of Pesticide Science*, 20(1): pp. 750–782 (Abstract), 1995.

Luyengi et al. "Rotenoids and Chalcones from Mundelea–Sericea that Inhibit Phorbol Ester–Induced Ornithine Decarboxylase Activity", *Phytochemistry*, 36(6): pp. 1523–1526 (Abstract), 1994.

Namgoong et al. "Effects of Naturally–Occurring Flavonoids on Mitogen–Induced Lymphocyte–Proliferation and Mixed Lymphocyte Culture", *Life Sciences*, 54(5): pp. 313–320 (Abstract), 1994.

Marshall, A.D. and Caldwell, J. "Influence of Modulators of Epoxide Metabolism on the Cytotoxicity of Trans–Anethole in Freshly Isolated Rat Hepatocytes", *Food and Chemical Toxicology*, 30(6): pp. 467–473 (Abstract), 1992.

Murakami et al. "Chalcone Tetramers, Lophirachalcone and Alatachalcone, from Dophira–Alata as Possible Antitumor Promoters", *Bioscience Biotechnology and Biochemistry*, 56(5): pp. 769–772 (Abstract), 1992.

Powers et al. "Automated Parallel Synthesis of Chalcone–Based Screening Libraries", *Tetrahedron*, 54: pp. 4085–4096, 1988.

Huang et al. "New Compounds with DNA Strand–Scission Activity from the Combined Leaf and Stem of *Uvaria hamiltonii*", *J. Nat. Prod.*, 61: pp. 446–450, 1998.

Herencia et al. "Synthesis and Anti–Inflammatory Activity of Chalcone Derivatives", *Bioorganic & Medicinal Chemistry Letters*, 8: pp. 1169–1174, 1998.

Herencia et al. "Novel Anti Inflammatory Chalcone Derivatives Inhibit the Induction of Nitric Oxide Synthase and Cyclooxygenase–2 in Mouse Peritoneal Macrophages", *FEBS Letters*, 453: pp. 129–134, 1999.

Severi et al. "Synthesis and Activity of a New Series of Chalcones as Aldose Reductase Inhibitors", *Eur. J. Med. Chem.*, 33: pp. 859–866, 1998.

Dinkova–Kostova et al. "Chemoprotective properties of Phenylpropenoids Bis(benzylidene) Cycloalkanones, and Related Michael Reaction Acceptors: Correlation of Potencies as Phase 2–Enzyme Inducers and Radical Scavengers", *J. Med. Chem.*, 41: pp. 5287–5296, 1998.

Edwards et al. "Chalcones: A New Class of Antimitotic Agents", *J. Med. Chem.*, 33: pp. 1948–1954, 1990.

Dimmock, J. R. et al., *J. Pharm. Sci* (1994), 83(6), 852–8, XP002180652, p. 853.

Dore, Jean C. et al., *Chim. Ther.* (1973), 8(2), 188–92, XP002108653, p. 189; Tables I,II.

Chemical Abstracts, vol. 131, No. 4, Jul. 26, 1999 Columbus, Ohio, US; abstract No. 39319, Sung, Nack–Do et al., XP002180655 abstract & Han'Guk Nonghwa Hakhoechi (1999), 42(1), 68–72.

Chemical Abstracts, vol. 115, No. 3, Jul. 22, 1991 Columbus, Ohio, US; abstract No. 21607, Dimmock, J. R. et al.: XP002180656, abstract, & Drug Res. Delivery 1990, 7(1), 45–49.

Chemical Abstracts, vol. 93, No. 22, Dec. 1, 1980, Columbus, Ohio, U.S. abstract No. 210256, Takeuchi, Setsuo, et al., AntiCancer pharmaceuticals, XP002180657 abstract & JP 55 045660 A (Institute of Physical and Chemical Research, Japan; Kaken Chemical Co., Mar. 31, 1980.

Chemical Abstracts, vol. 121, No. 16, Oct. 17, 1994, Columbus, Ohio, US; abstract No. 187293, Shibata, Shoji, et al., "Anticancer agents containing chalcones" XP002180658 abstract & JP 06 122623 A (Minophagen Pharm Co., Japan) May 6, 1994.

Iwata, Susumu, et al., "Antitumorigenic Activities of Chalcones. I. Inhibitory Effects of Chalcone Derivatives on P–32–Incorporation into Phospholipids of HeLa Cells Promoted by 1 2–O–Tetradecanoyl–phorbol 13–Acetate (TPA)", Biol. Pharm. Bull. (1995), 18(12), 1710–13 XP002180654.

Anto, RJ et al., "Anticancer and antioxidant activity of synthetic chalcones and related compounds", Cancer Letters 1995, 97, 33–37.

Arbiser, JL et al., "Curcumin Is an In Vivo Inhibitor of Angiogenesis", Molecular Medicine 1998, 4, 376–383.

Artico, M et al., "Geometrically and Conformationally Restrained Cinnamoyl Compounds as Inhibitors of HIV_1 Integrase: Synthesis, Biological Evaluation, and Molecular Modeling",J. Med. Chem. 1998, 41, 3948–3960.

Bois, F et al., "Synthesis and Biological Activity of 4–Alkoxy Chalcones: Potential Hydrophobic Modulators of P–Glycoprotein–Mediated Multidrug Resistance",Bioorganic & Med. Chem. 1999, 7, 2691–2695.

Buolamwini, JK et al., "CoMFA and CoMSIA 3D QSAR and Docking Studies on Conformationallly–Restrained Cinnamoyl HIV-1 Integrase Inhibitors: Exploration of a Binding Mode at the Active Site",J. Med. Chem. 2002, 45, 841–852.

Deshpande, AM et al., "Synthesis and Screening of a Combinatorial Library of Naphthalene Substituted Chalcones: Inhibitors of Leukotriene B4", Bioorganic & Med. Chem. 1999, 7, 1237–1240.

Dimmock, J et al. "Conformational and Quantitative Structure–Activity Relationship Study of Cytotoxic 2–Arylidenebenzocycloalkanones",J. Med. Chem. 1999,42, 1358–1366.

Dimmock, J et al., "Cytotoxic 2,6–bis(arylidene)cyclohexanones and related compounds", Eur. J. Med. Chem. 2000, 35, 967–977.

Dimmock, J et al. , "A Conformational and Structure–Activity Relationship Study of Cytotoxic 3,5–Bis(arylidene)–4–piperidones and Related N–Acryloyl Analogues"J. Med. Chem. 2001, 44,586–593.

Dinkova–Kostova, et al. "Potency of Michael reaction acceptors as inducers of enzymes that protect against carcinogenesis depends on their reactivity with sulfhydryl groups", PNAS 2001, 98, 3404–3409.

Dixon, R et al., "Flavonoids and isoflavonoids–a gold mine for metabolic engineering", Trends in Plant Science,1999, 4, 394–400.

Hall, I et al., "Cycloalkanones. 4. Antifertility Activity", J. Med. Chem. 1974, 17, 1253–1257.

Iwata, S et al., "Antitumorigenic Activities of Chalcones (II). Photo–isomerization of Chalcones and the Correlation with Their Biological Activities", Biol. Pharm. Bull. 1997, 20(12), 1266–1270.

Iwata, S et al., "Inhibitory Effect of Chalcone Derivatives on Recombinant Human Aldose Reductase", Biol. Pharm. Bull. 1999, 22(3), 323–325.

Jovanovic, BZ et al., "C–13 NMR spectra of pyridine chalcone analogs" J. Molecular Structure 1999,482–483, 371–374.

Kamei, H et al., "Tumor Cell Growth Suppression by Chalcone (1,3–Diphenyl–2–Propen–1 –One)", Cancer Biother. Rapidpharm. 1997,12,51–54.

Laliberte, R et al., "Anthelmintic Activites of Chalcones and Related Compounds"Canadian J. Pharm. Sci. 1967, 37–43.

Lawrence, N et al., "The Interaction of Chalcones with Tubulin", Anti–Cancer Drug Design 2000, 15, 135–141.

Lawrence, N et al., "Linked Parallel Synthesis and MTT Bioassay Screening of Substituted Chalcones", J. Comb. Chem. 2001, 3, 421–426.

Li, R et al., "In Vitro Antimalarial Activity of Chalcones and Their Derivatives", J. Med. Chem. 1995, 38, 5031–5037.

Liu, M et al., "Antimalarial Alkoxylated and Hydroxylated Chalones: Structure–Activity Relationship Analysis" J. Med. Chem. 2001, 44, 4443 –4452.

Mamolo, MG et al., "Synthesis and antimycobacterial activity of some N1–[1–{3–aryl–1–(pyridin–2–, 3–, or 4–yl)–3–oxo}propyl]–2–pyridinecarboxamidrazones", Il Farmaco 1999,54, 761–767.

Motohashi, N et al., "Antimutagenic effects of dehydrozingerone and its analogs on UV–induced mutagenesis in Escherichia coli", Mutation Research 1997, 377, 17–25.

Motohashi, N et al., "Structure–antimutagenic activity relationships of benzalacetone derivatives against UV–induced mutagenesis in E. coli WP2uvrA and 1–induced mutagenesis in Salmonella typhimurium TA2638", Mutation Research 2001. 474, 113–120.

Murakami, M et al., "Chalcone Tetramers, Lophirachalcone and Alatachalcone, from Lophira alata as Possible Anti–tumor Promoters", J. Biotech. Biochem. 1992, 56, 769–772.

Niesen, SF et al., "Modifications of the alpha,beta–Double Bond in Chalcones only Marginally Affect the Antiprotozoal Activities", Bioorganic & Med. Chem. 1998, 6, 937–945.

Nielsen, S et al., "Antileishmanial Chalcones: Statistical Design, Synthesis, and Thrree–Dimensional Quantitative Structure–Activity Relationship Analysis", J. Med. Chem. 1998, 41,4819–4832.

Parmar, V et al., "Anti–invasive Activity of Alkaloids and Polyphenolics in Vitro", Bioorganic & Med. Chem. 1997, 5, 1609–1619.

Piantadosi, C et al., "Cycloalkanones. 2. Synthesis and Biological Activity of alpha,alpha'–Dibenzylcycloalkanones"J. Med. Chem. 1973, 16, 770–775.

Pouget, C et al., "Flavonoids: Structural Requirements for Antiproliferative Activity on Breast Cancer Cells", Bioorganic & Med. Chem. Ltrs. 2001, 11, 3095–3097.

Satomi, Y, "Inhibitory Effects of 3'–Methyl–3–Hydroxy–Chalcone on Proliferation of Human Malignant Tumor Cells and on Skin Carcinogenesis", Int. J. Cancer 1993, 55, 506–514.

Shibata, S et al., "Inhibitory Effects of Licochalcone A Isolated from Glycyrrhiza inflata Root on Inflammatory Ear Edema and Tumour Promotion in Mice", Planta Med. 1991, 57, 221–224.

* cited by examiner (1)

(2)

(3)

(4)

(5)

(6)

(7)

(8)

(9)

(10)

Compounds 1-10 from Table 1

Compounds 11-16 from Table 1

Compounds 17-26 from Table 2

(27)

(28)

(29)

(30)

Compounds 27-30 from Table 2

(31)

(32)

(33)

(34)

(35)

(36)

Compounds 31-36 from Table 3

(37)

(38)

(39)

(40)

(41)

(42)

Compounds 37-42 from Table 3

(43)

(44)

(45)

(46)

Compounds 43-46 from Table 4

(47)

(48)

(49)

(50)

Compounds 47-50 from Table 4

(51)  (52)
(53)  (54)

Compounds 51-54 from Table 5

Compound 55-64 from Table 5

(65)

(66)

(67)

(68)

(69)

(70)

(71)

Compounds 65-71 from Table 5

Compounds 72-79 from Table 6

SVR Cell Growth Inhibition
1,3,6 ug/ml or 3,6,9 ug/ml (See Table 1-6)

SVR Cell Growth Inhibition
1.3.6 ug/ml or 3.6.9 ug/ml (See Table 1-6)

CHALCONE AND ITS ANALOGS AS AGENTS FOR THE INHIBITION OF ANGIOGENESIS AND RELATED DISEASE STATES

RELATED APPLICATIONS

This application is a division of application Ser. No. 09/748,599, filed Dec. 26, 2000, now U.S. Pat. No. 6,462,075 which claims priority from provisional application Ser. No. 60/171,883 filed Dec. 23, 1999.

FIELD OF THE INVENTION

The present invention relates to chalcone and chalcone derivatives and analogs which are useful as angiogenesis inhibitors. The present compounds, which are inexpensive to synthesize exhibit unexpectedly good activity as angiogenesis inhibitors. The present invention also relates to the use of chalcone and its analogs as antitumor/anticancer agents and to treat a number of conditions or disease states in which angiogenesis is a factor.

BACKGROUND OF THE INVENTION

Chalcone is a member or derivative of the phenylypropanoids, a large group of phenolic compounds synthesized only in plants, and predominantly derived from the aromatic amino acid phenylalanine. Phenylpropanoids and their derivatives perform diverse physiological functions in plants, and are represented by the polymeric lignins, the coumarins, suberins, stilbenes and flavonoids, as well as the chalcones, sometimes considered a sub-class of the flavonoids. In the predominant form of lignins, phenylpropanoids are second only to cellulose among the biomolecules in total biosphere abundance. Lignins have a primarily structural role, but many compounds in this versatile group are biochemically active. The flavonoids, for example

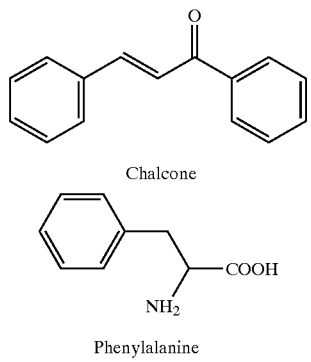

serve in many species as attractants of pollinators, UV protectors, insect repellents, signalling molecules and antibiotics, while the coumarins and stilbenes are implicated in the defense response of plants to pathogen ingress via their anti-microbial function effect.

Considering the other leg of the background of the present invention, angiogenesis may be defined as the development of a blood supply to a given area of tissue. The development of a blood supply may be part of normal embryonic development, represent the revascularization of a wound bed, or involve the stimulation of vessel growth by inflammatory or malignant cells. Sometimes angiogenesis is defined as the process through which tumors or inflammatory conditions derive a blood supply through the generation of microvessels. Although it may seem unremarkable that new growth of soft tissue requires new vascularization, the concept of angiogenesis as a key component of tissue growth and in particular, a key point of intervention in pathological tissue growth, had initially met with skepticism. By now the idea is well accepted.

Tumors need to induce formation of blood vessels to grow beyond a small size. A small tumor can use diffusion from nearby capillaries as its source of oxygenation, nutrition, and waste removal. However, once a tumor exceeds a critical mass, the center of the tumor becomes necrotic, because these crucial functions are no longer available. When a tumor gains the ability to generate new blood vessels, perfusion of a larger tumor mass is possible. The ability of malignant cells to form a large tumor and to metastasize is accompanied by decreased cellular differentiation and increased ability to produce angiogenic factors. Hence there is a strong interest in compounds that block angiogenesis and interrupt the growth process of malignant tumors, inflammatory lesions and benign neoplasms, as well as in compounds which stimulate cellular differentiation, and impede metastasis.

A tumor's ability to become neovascularized permits rapid tumor growth and increases the likelihood of metastases; the transition from a quiescent tumor to an invasive tumor is accompanied by the crucial acquisition of angiogenic properties. The critical point may be characterized as the activation of a specific angiogenic switch. The phenotypic change from quiescence to virulence likely requires a change in the balance of angiogenic simulators and angiogenic inhibitors. The nature of the angiogenic switch is not known, however, growth factors and signal transduction are expected to be key components in the investigation of angiogenic regulatory mechanisms.

The first angiogenesis factor isolated was basic fibroblast growth factor (bFGF). Others include vascular endothelial growth factor (VEGF), interleukin-8, hepatocyte growth factor, platelet derived endothelial growth factor (PD-ECGF), and corticotropin-releasing hormone (CRH). The discovery of endogenous angiogenesis simulators naturally led researchers to ask whether there existed endogenous angiogenesis inhibitors. Interferon-alpha, which inhibits the replication of primary endothelial cells, was the first endogenous angiogenesis inhibitor discovered. Other naturally occurring small molecules which have been discovered to have anti-angiogenic activity include the retinoids and curcumin, a small molecular weight compound which is isolated from the commonly used spice turmeric. In animal models, curcumin and its derivatives have been shown to inhibit the progression of chemically induced colon and skin cancers. A summary of some major known angiogenesis stimulators and inhibitors is shown below.

| Angiogenesis Simulators | Angiogenesis Inhibitors |
| --- | --- |
| Basic fibroblast growth factor (bFGF) | Angiostatin |
| Vascular endothelial growth factor (VEGF) | Endostatin |
| Prostaglandin E2 | Curcumin |
| Hepatocyte growth factor | Fumagillin derivatives |
| Proliferin | Proliferin-related peptide |
| Nitric oxide | Nitric oxide inhibitors |
| Integrins ($\alpha v\beta_3$, $\alpha v\beta_4$) | Phosphatidylinositol-3-kinase inhibitors |
| Corticotropin-releasing hormone | Thalidomide |
| Interleukin-8 | Interleukin-12 |
| Platelet derived endothelial growth factor | Farnesyltransferase inhibitors |
| protaglandin | retinoids |
|  | alpha interferon |

Among the angiogenisis inhibitors, retinoids (vitamin A and its derivatives) play an important role in the development and differentiation of epidermal cells, as well as in reversing precancerous lesions. A number of references disclose retinoids being used in cancer prophylaxis and as inducers of cell differentiation. Kizaki et al., *Seminars in Oncology* 19(1):95–105(1992), for example, report that retinoids are potential anti-carcinogenic agents in many experimental models and that they inhibit growth and induce differentiation in transformed neoplastic cells. Unfortunately, the retinoids have a significant level of toxicity and administration of the known retinoid agents at therapeutic doses may be associated with undesirable side effects including headache, teratogenesis, mucocutaneous toxicity, musculoskeletal toxicity, dylipidemias, skin irritation, headache and hepatotoxicity. Accordingly, there exists a need to provide novel compounds having retinoid activity but which have less toxicity and/or side effects.

Chalcone compounds (3-oxo-1-propenyl derivatives) are sometimes classified as derivatives of the retinoids, and also of the flavones or flavonoids. Some flavones and chalcones have been found to have anti-tumor properties. Compounds related to coumarin, a flavone isolate from the widely used spice turmeric, are known to inhibit the carcinogenicity of carcinogens: Coumarin has been tested for treatment of melanoma. Certain chalcones and flavonoids, including biochanin A, are also known to exhibit anti-mitotic action in inhibiting cell division; e.g. in Shibata, *Anti-tumorgenic chalcones*, Stem Cells, 12:44–62, 1994; Edwards et al., *Chalcones: A New Class of Antimitotic Agents*, J. Med. Chem., 33:1948–1954, 1990; and Varma, *Dietary Bioflavonoids, Chalcones and Related Alkenones in Prevention and Treatment of Cancer*, Nutrition, 12; 643 (1996).

OBJECTS OF THE INVENTION

It is an object of the invention to provide compounds and pharmaceutical compositions which exhibit activity as inhibitors of angiogenesis.

It is another object of the invention to provide compounds and pharmaceutical compositions which can be used to treat tumors and/or cancer.

It is an additional object of the present invention to provide compounds and pharmaceutical compositions for use in treating angiogenic skin disorders such as psoriasis, venous ulcers, acne, rosacea, warts, eczema, hemangiomas, lymphangiogenesis, among numerous others, as well as internal malignancies (e.g., colon, cervical, bladder), oral malignancies, cutaneous malignancies, including basal cell carcinoma, squamous cell carcinoma and melanoma and inflammation.

It is yet another object of the invention to provide a method of treating tumors and/or cancer as well as the above-referenced angiogenic skin disorders It is still another object of the present invention to provide compounds which exhibit anti-angiogenesis and/or anti-tumor activity and are relatively inexpensive to synthesize.

It is yet another object of the invention to enhance the inhibition of Map kinase and the phosphoinositide cascade.

Any one or more of these and/or other objects of the present invention may be readily gleaned from a description of the invention which follows.

BRIEF SUMMARY OF THE INVENTION

The present invention relates to compounds or pharmaceutically acceptable salts, thereof of the formula:

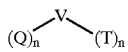

Where n is 0, 1 or 2;

Q and T are independently selected from a chemical group of the formula:

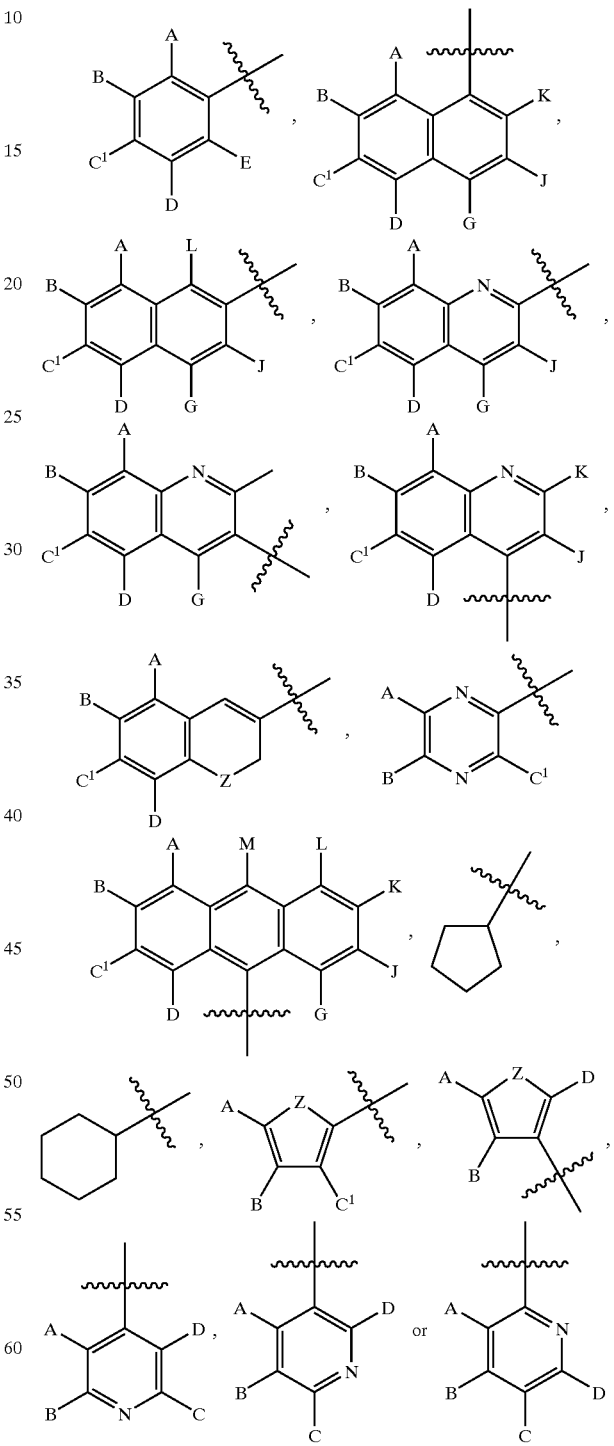

Where A, B, $C^1$, D, E, G, J, K, L and M are independently selected from H, a $C_1$–$C_3$ alkyl group, a halogen, an OR group, COOH, COOR$_1$, an alkylene ester group according to the structure —(CH$_2$)$_m$COOR$_1$ or a CF$_3$ group;

R is a C$_1$–C$_4$ alkyl group (preferably, C$_1$–C$_3$ alkyl), a benzyl or phenyl group or a

group;

R$_1$ is a C$_1$–C$_{20}$ alkyl group, preferably a C$_1$–C$_3$ alkyl group;
R$_2$ is a C$_1$–C$_{20}$ alkyl group, preferably a C$_1$–C$_3$ alkyl group;
Z is O, S, N—H, NCH$_3$, NCH$_2$CH$_3$, or CH$_2$;
V is a group according to the structure:

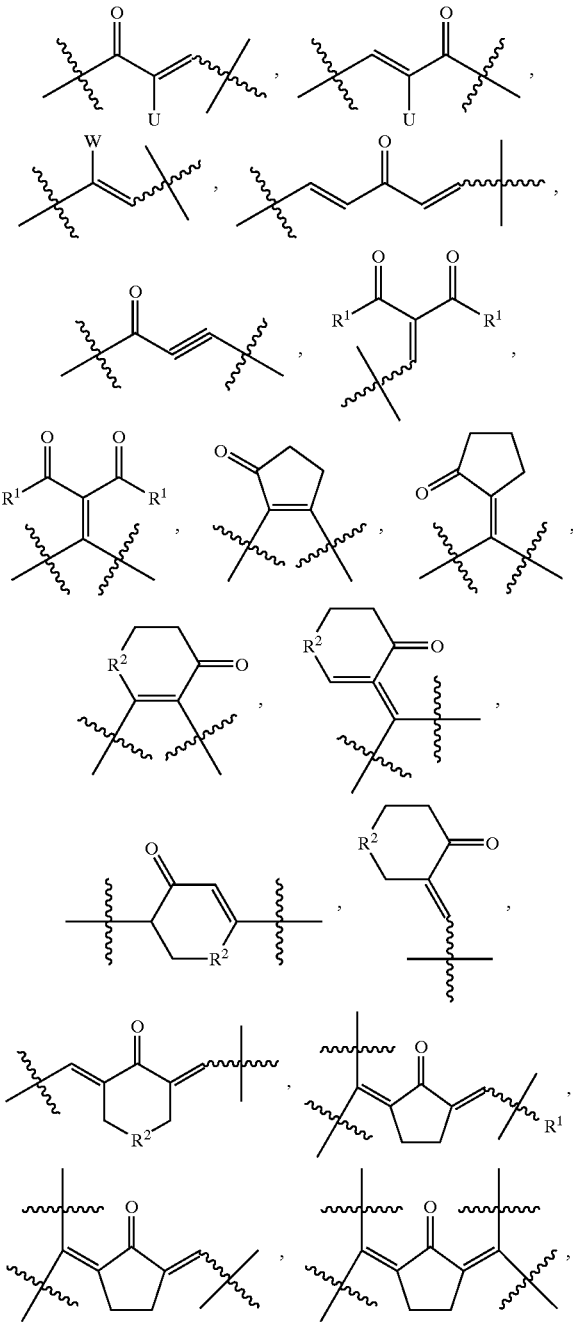

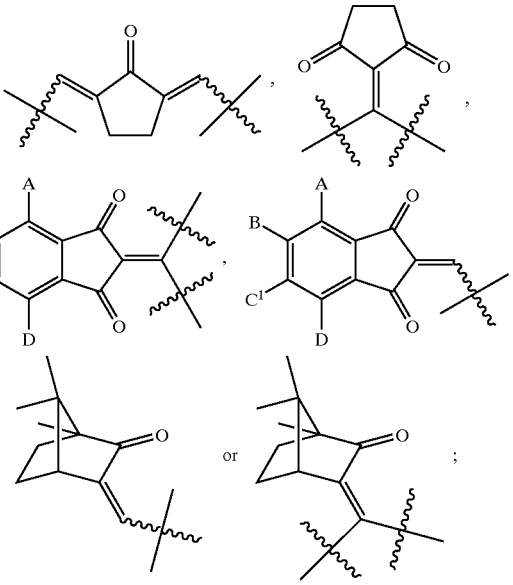

Where A, B, C$^1$, D and Y are the same as set forth above;
U is H or halogen;
W is COR$^1$, CN or COOR$^1$;
R$^1$ is a C$_1$–C$_4$ alkyl group (preferably, a C$_1$–C$_3$ alkyl group) or a benzyl or phenyl group;
R$^2$ is O, S, NH, NCH$_3$, NCH$_2$CH$_3$, or CH$_2$;
With the proviso that n is not 0 for both Q and T and when n is 1 for Q and T, Q-V or V-T may together form a structure according to the formula:

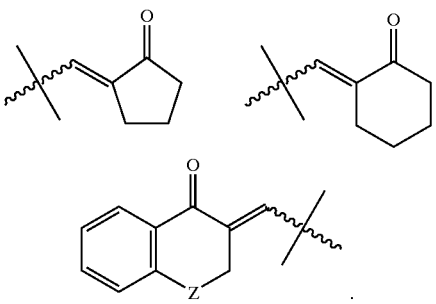

Where Z is the same as set forth above.

The present invention is also directed to pharmaceutical compositions comprising an effective amount of one or more compounds according to the present invention (including a pharmaceutically acceptable salt, thereof), optionally in combination with a pharmaceutically acceptable carrier, excipient or additive.

The present invention is also directed to methods for the treatment of tumors and/or cancer, internal and oral malignancies, angiogenic skin disorders and inflammation, including chronic inflammatory disease comprising administering an effective amount of one or more compounds according to the present invention to a patient in need of therapy, thereof.

More particularly, the present invention relates to methods for inhibiting the growth of neoplasia, including a malignant tumor or cancer comprising exposing the neoplasia to an inhibitory or therapeutically effective amount or concentration of at least one of the disclosed compounds. This method may be used therapeutically, in the treatment of neoplasia, including cancer or in comparison tests such as assays for determining the activities of related analogs as well as for determining the susceptibility of a patient's cancer to one or more of the compounds according to the present invention. Treatment of internal malignancies such as eye or ocular cancer, rectal cancer, colon cancer, cervical cancer, prostate cancer, breast cancer and bladder cancer, among numerous others, and oral malignancies are also contemplated by the present invention.

Methods for treating angiogenic skin disorders such as psoriasis, acne, rosacea, warts, eczema, hemangiomas, lymphangiogenesis as well as inflammation such as chronic inflammatory disease, including arthritis, lupus and scleroderma are also contemplated by the present invention, such methods comprising administering a therapeutically effective amount of one or more of the disclosed compounds to a patient in need of such treatment.

DETAILED DESCRIPTION OF THE INVENTION

Figure 1:
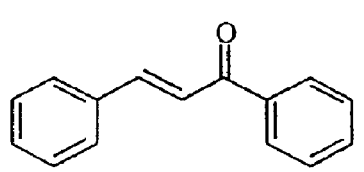
FIGS. 1–12 are representative of the chemical compounds which are tested and presented in Tables 1–6.
Figure 1:
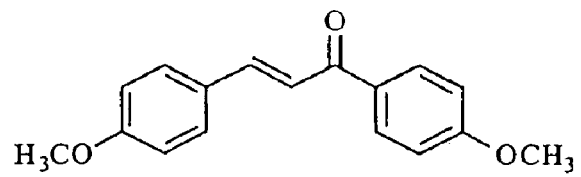
Figure 1:
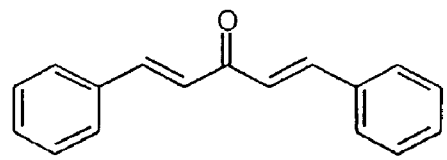
Figure 1:
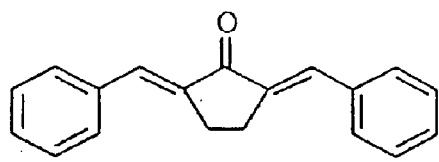
Figure 1:
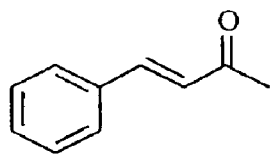
Figure 1:
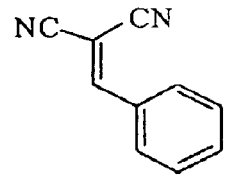
Figure 1:
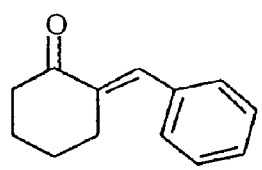
Figure 1:
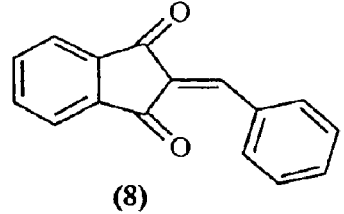
Figure 1:
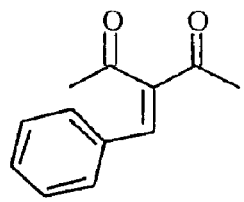
Figure 1:
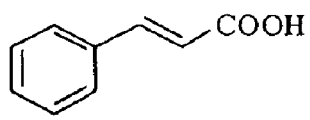
Figure 2:
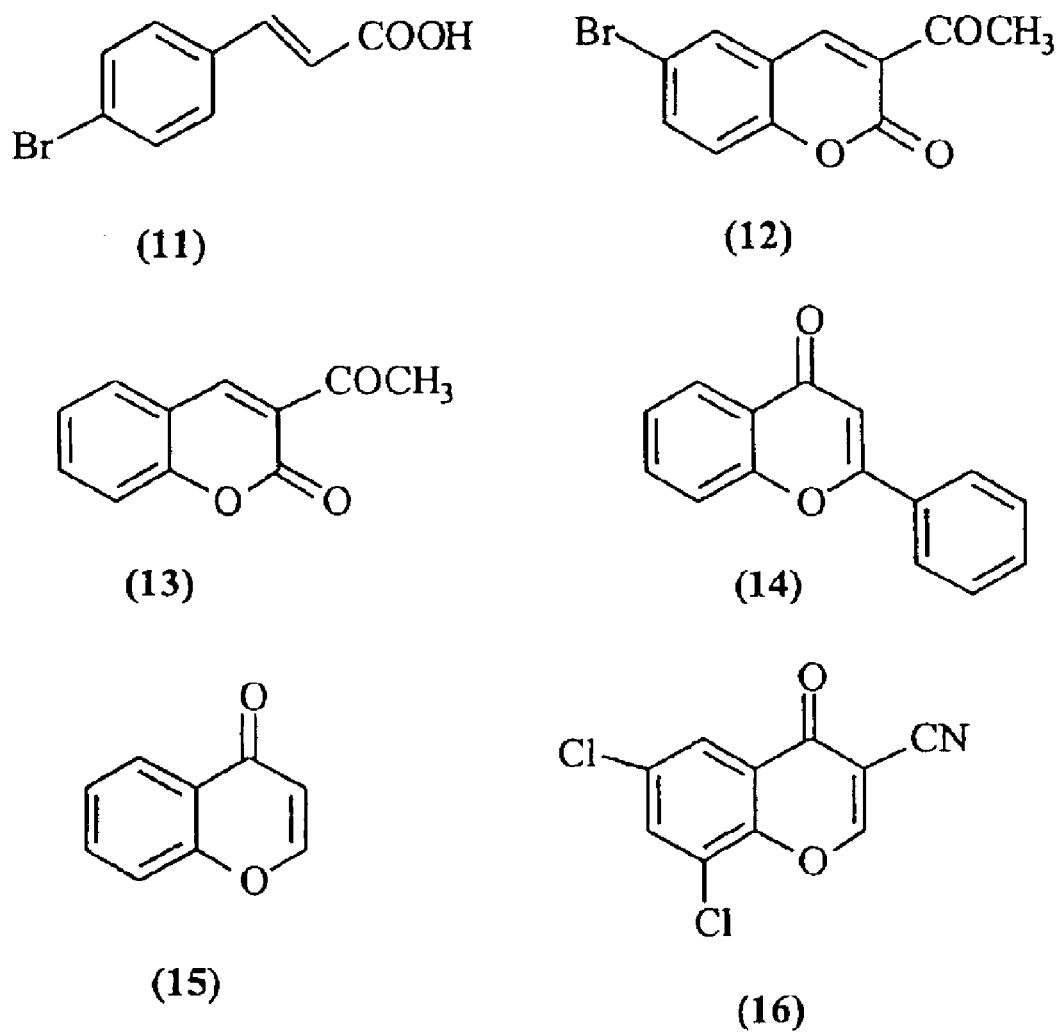
Figure 3:
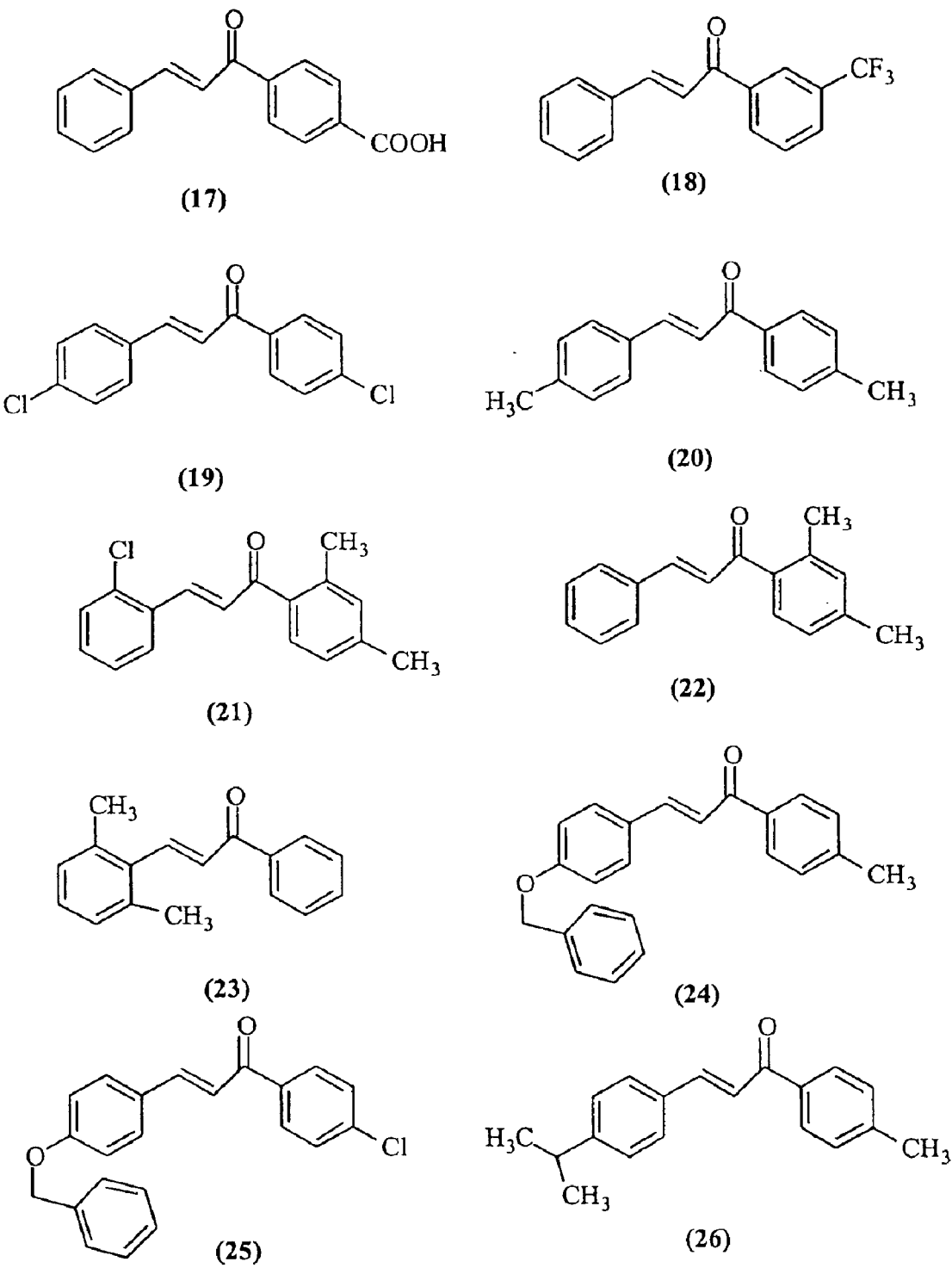
Figure 4:
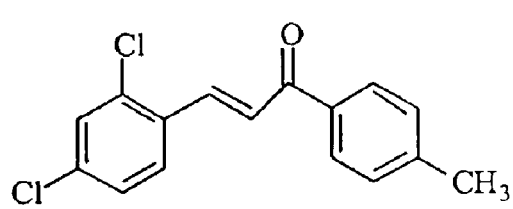
Figure 4:
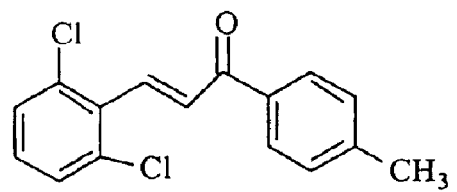
Figure 4:
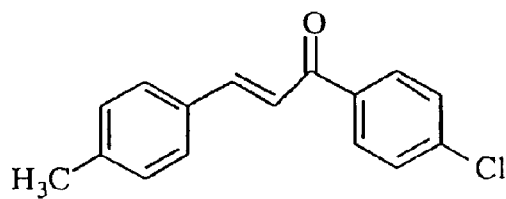
Figure 4:
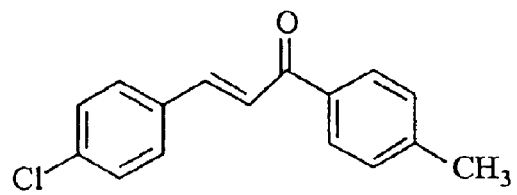
Figure 5:
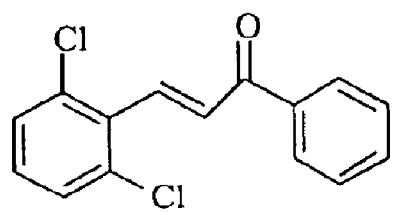
Figure 5:
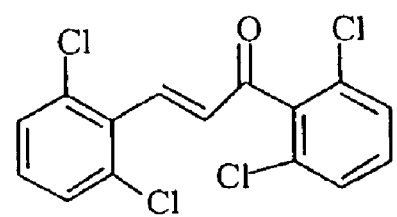
Figure 5:
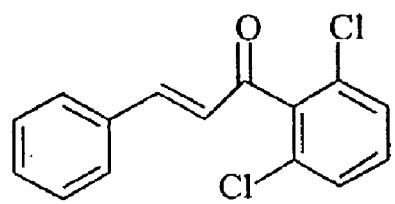
Figure 5:
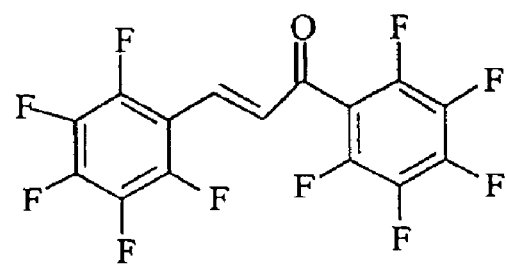
Figure 5:
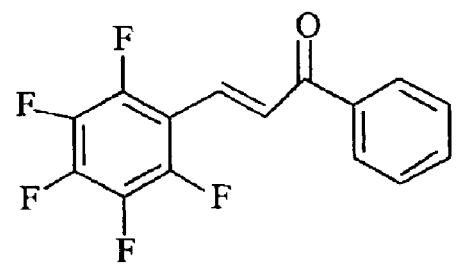
Figure 5:
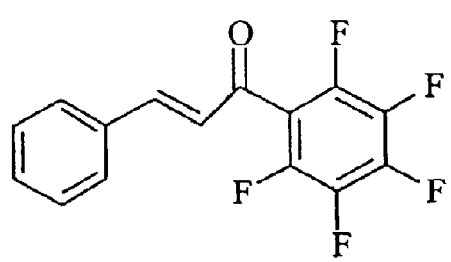
Figure 6:
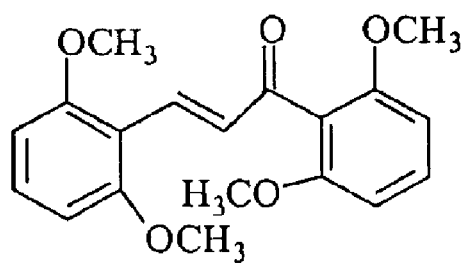
Figure 6:
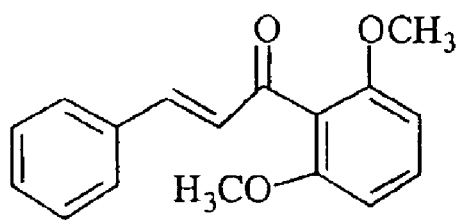
Figure 6:
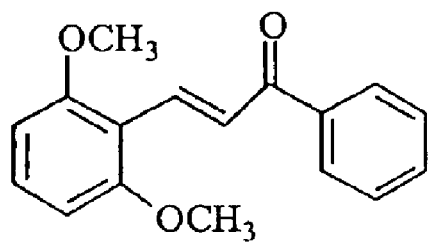
Figure 6:
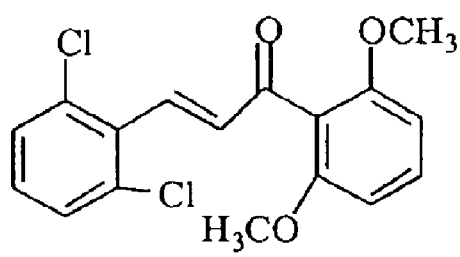
Figure 6:
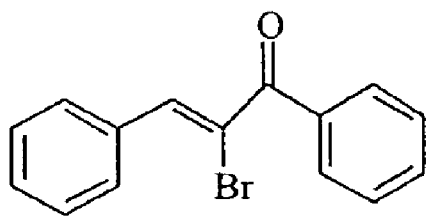
Figure 6:
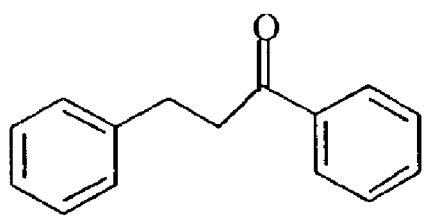
Figure 7:
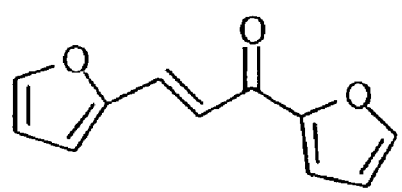
Figure 7:
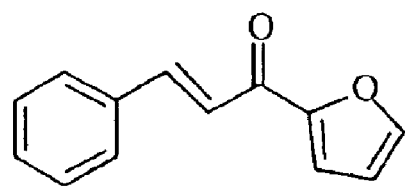
Figure 7:
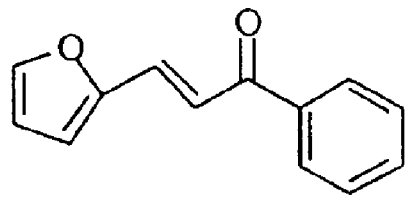
Figure 7:
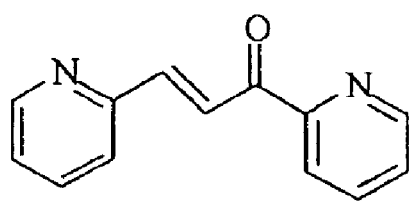
Figure 8:
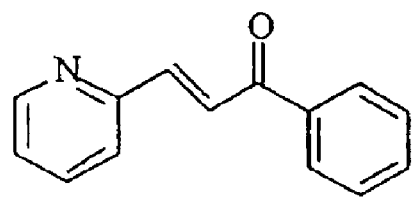
Figure 8:
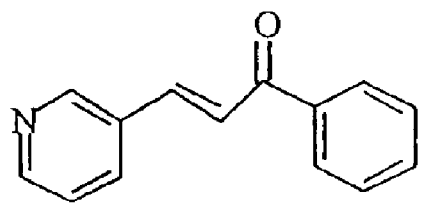
Figure 8:
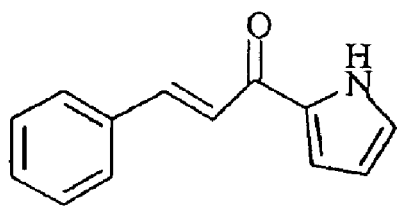
Figure 8:
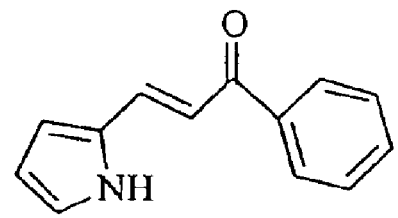
Figure 9:
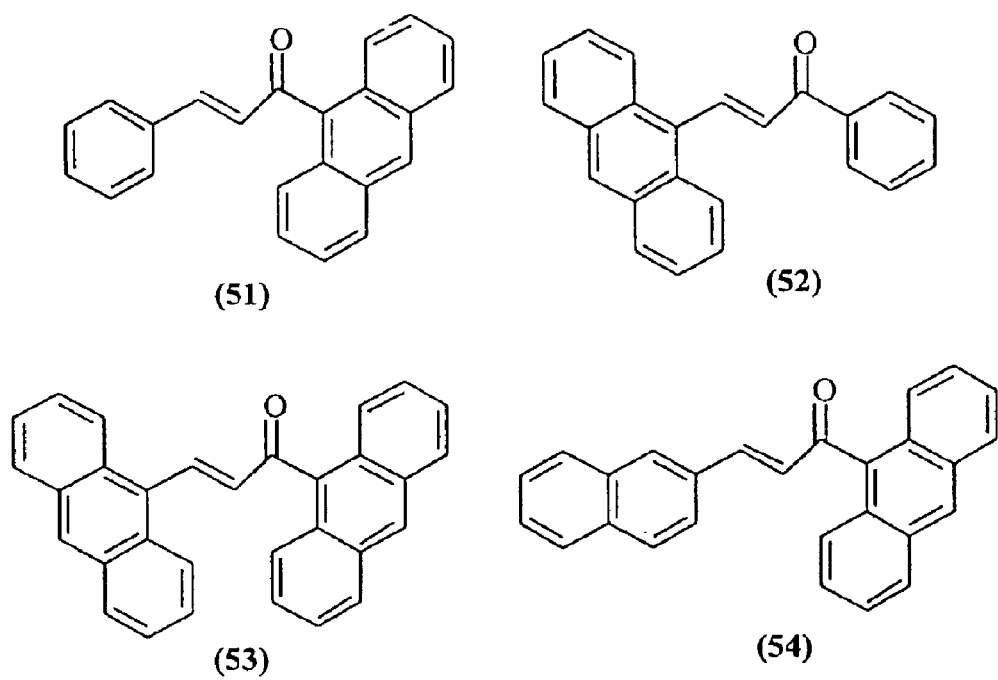
Figure 10:
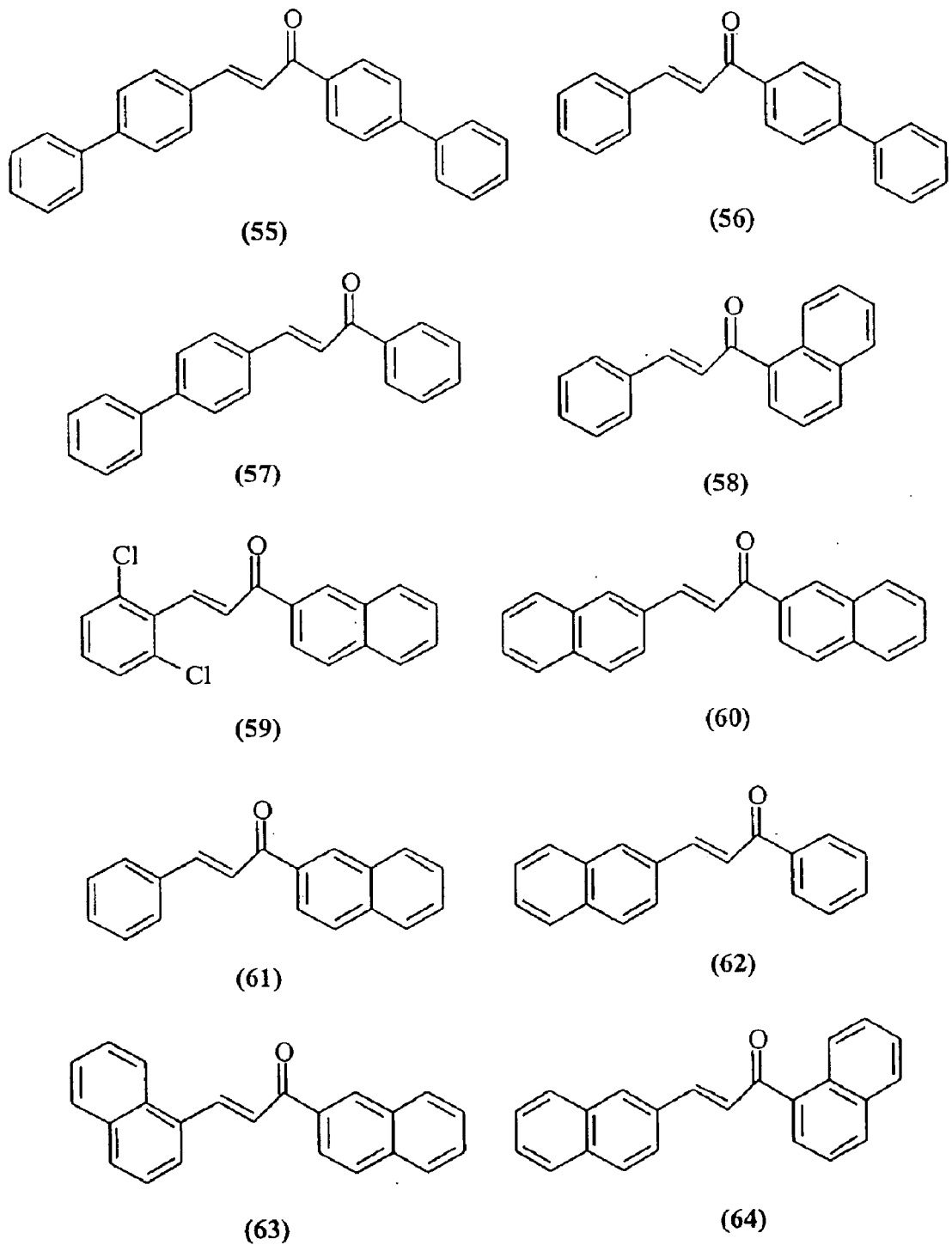
Figure 11:
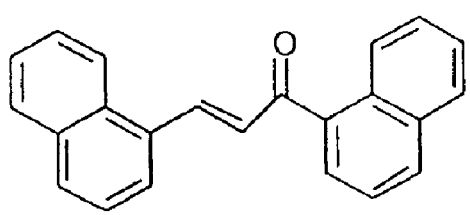
Figure 11:
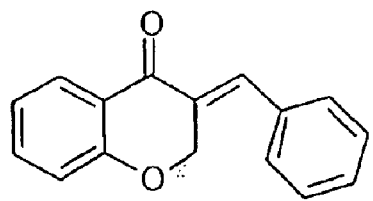
Figure 11:
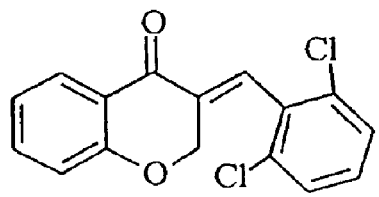
Figure 11:
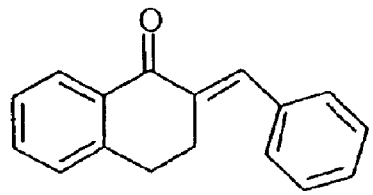
Figure 11:
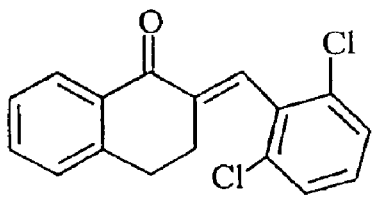
Figure 11:
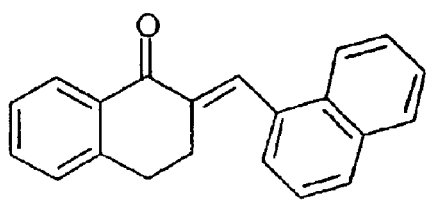
Figure 11:
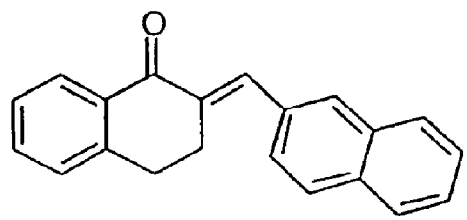
Figure 12:
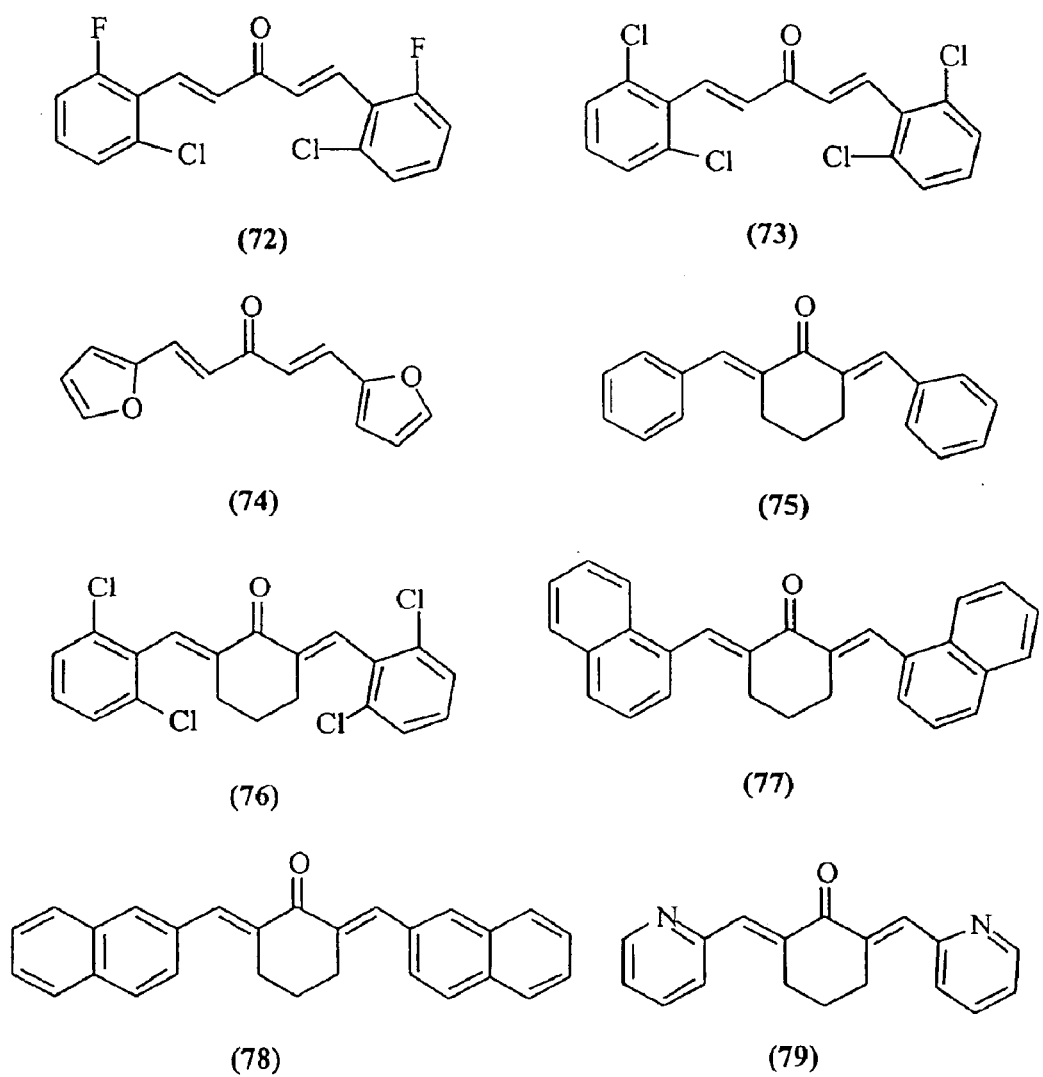

The following terms shall be used throughout the specification to describe the present invention.

The term "patient" is used throughout the specification to describe an animal, preferably a human, to whom treatment, including prophylactic treatment, with the compounds according to the present invention is provided. For treatment of those infections, conditions or disease states which are specific for a specific animal such as a human patient, the term patient refers to that specific animal. In most instances, the term patient refers to a human patient.

The term "effective amount" is used throughout the specification to describe concentrations or amounts of compounds according to the present invention which may be used to produce a favorable change in the disease or condition treated, whether that change is a remission, a decrease in growth or size of cancer, tumor or other growth, a favorable physiological result including the clearing up of skin or tissue, or the like, depending upon the disease or condition treated.

The term "angiogenesis" is used throughout the specification to describe the biological processes which result in the development of blood vessels or increase in the vascularity of tissue in an organism. With respect to the present invention, the term angiogenesis is defined as the process through which tumors or other rapidly proliferating tissue derive a blood supply through the generation of microvessels.

The term "tumor" is used to describe an abnormal growth in tissue which occurs when cellular proliferation is more rapid than normal tissue and continues to grow after the stimuli that initated the new growth cease. Tumors generally exhibit partial or complete lack of structural organization and functional coordination with the normal tissue, and usually form a distinct mass of tissue which may be benign (benign tumor) or malignant (carcinoma). Tumors tend to be highly vascularized. The term "cancer" is used as a general term herein to describe malignant tumors or carcinoma. These malignant tumors may invade surrounding tissues, may metastasize to several sites and are likely to recur after attempted removal and to cause death of the patient unless adequately treated. As used herein, the terms carcinoma and cancer are subsumed under the term tumor.

The terms "angiogenic disease", "angiogenic disorder" and "angiogenic skin disorder" is used throughout the specification to describe a disorder, generally a skin disorder or related disorder which occurs as a consequence of or which results in increased vascularization in tissue. Oftentimes, the etiology of the angiogenic disease is unkown. However, whether angiogenesis is an actual cause of a disease state or is simply a condition of the disease state is unimportant, but the inhibition of angiogenesis in treating or reversing the disease state or condition is an important aspect of the present invention. Examples of angiogenic skin disorders which may be treated utilizing compounds according to the present invention include, for example, psoriasis, acne, rosacea, warts, eczema, hemangiomas and lymphangiogenesis, among numerous others, including Sturge-Weber syndrome, neurofibromatosis, tuberous sclerosis, chronic inflammatory disease and arthritis. Any skin disorder which has as a primary or secondary characterization, increased vascularization, is considered an angiogenic skin disorder for purposes of the present invention and is amenable to treatment with compounds according to the present invention.

The term "rosacea" is used to describe acne rosacea or erythematosa characterized by vascular and follicular dilation involving the nose and contiguous portions of the cheeks. Rosacea may vary from very mild but persistent erythema to extensive hyperplasia of the sebaceous glands with deep-seated papules and pustules and accompanied by telangiectasia at the affected erythematous sites. Also called hypertrophic rosacea or rhinophyma, depending upon the severity of the condition.

The term "wart" is used to describe a small, usually hard tumerous growth on the skin. Also known as a verrucas, a wart is a flesh-colored growth of the skin which is characterized by circumscribed hypertrophy of the papillae of the corium, with thickening of the malpighian, granulation and keratin layers of the epidermis. Verucca vulgaris, a subset of warts or verruca, is characterized by infection of the keratinocytes with human papillomavirus.

The term "psoriasis" is used to describe a skin condition which is characterized by the eruption of circumscribed, discrete and confluent, reddish, silvery-scaled maculopapules; the lesions occur preeminently on the elbows, knees, scalp and trunk and microscopically show characteristic parakeratosis and elongation of rete ridges.

The term "acne" is used to describe a condition of the skin characterized by inflammatory follicular, papular and pustular eruptions involving the sebaceous apparatus. Although there are numerous forms of acne, the most common form is known as acne simplex or acne vulgaris which is characterized by eruptions of the face, upper back and chest and is primarily comprised of comedones, cysts, papules and pustules on an inflammatory base. The condition occurs primarily during puberty and adolesence due to an overactive sebaceous apparatus which is believed to be affected by hormonal activity.

The term "eczema" is a generic term used to describe acute or chronic inflammatory conditions of the skin, typically erythematous, edematous, papular, vesicular, and crusting; followed often by lichenification and scaling and occasionally by duskiness of the erythema and, infrequently, hyperpigmentation. Eczema is often accompanied by the sensation of itching and burning. Eczema vesicles form by intraepidermal spongiosis. Eczema is sometimes referred to colloquially as tetter, dry tetter and scaly tetter. There are numerous subcategories of eczema, all of which are treated by one or more of the compounds according to the present invention.

The symbols:

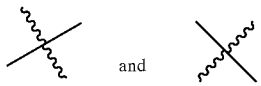

are used throughout the specification to depict a point at which a bond between a Q group and a V group or a T group and an V group in a Q-V-T compound according to the present invention occurs.

The symbol:

signifies that the stereochemistry of the bond that is made between groups is fixed (i.e., there cannot be more than one type of bond between the groups).

The symbol:

signifies that the stereochemistry of the bond that is made between groups is not fixed and is generally more than one type of bond (e.g., a cis and/or trans bond about a double bond). In general, all stereoisomers about a bond are disclosed using this symbol.

The compounds of the present invention are used to treat benign and malignant tumors, including various cancers such as, cervical, anal and oral cancers, stomach, colon, bladder, rectal, liver, pancreatic, lung, breast, cervix uteri, corpus uteri, ovary, prostate, testis, renal, brain/cns (e.g., gliomas), head and neck, eye or ocular, throat, skin melanoma, acute lymphocytic leukemia, acute myelogenous leukemia, Ewing's Sarcoma, Kaposi's Sarcoma, basal cell carinoma and squamous cell carcinoma, small cell lung cancer, choriocarcinoma, rhabdomyosarcoma, angiosarcoma, hemangioendothelioma, Wilms Tumor, neuroblastoma, mouth/pharynx, esophageal, larynx, kidney and lymphoma, among others. In addition, conditions such as neurofibromatosis, tuberous sclerosis (each of which conditions produces benign tumors of the skin), hemangiomas and lymphangiogenesis, among others, may be treated effectively with compounds according to the present invention.

Methods of treating tumors and/or cancer according to the present invention comprise administering to a patient in need thereof an effective amount of one or compounds according to the present invention.

A method of treating angiogenic skin disorders including psoriasis, acne, rosacea, warts and eczema, among numerous others, including Sturge-Weber syndrome, and related conditions using one or more of the disclosed compositions are other inventive aspects of the present invention. In addition, the present compounds may be used to treat venous ulcers of the skin as well. These methods comprise administering an effective amount of at least one compound according to the present invention to a patient in need of treatment or therapy.

Further inventive aspects of the present invention relate to the use of the present compositions in the treatment of arthritis and chronic inflammatory diseases, including rheumatoid arthritis and osteoarthritis, among others, including lupus and scleroderma. These methods also are directed to the administration of effective amounts of at least one compound according to the present invention to a patient in need of treatment or therapy.

Pharmaceutical compositions based upon these novel chemical compounds comprise the above-described compounds in a therapeutically effective amount for the treatment of a condition or disease such as neoplasia, including cancer, an angiogenic skin disease or an inflammatory disease or a related condition or disease optionally in combination with a pharmaceutically acceptable additive, carrier or excipient.

Certain of the compounds, in pharmaceutical dosage form, may be used as prophylactic agents for preventing a disease or condition from manifesting itself. In certain pharmaceutical dosage forms, the pro-drug form of the compounds according to the present invention may be preferred. In particular, prodrug forms which rely on $C_1$ to $C_{20}$ ester groups or amide groups (preferably a hydroxyl, free amine or substituted nitrogen group) which may be transformed into, for example, an amide or other group may be particularly useful in this context.

The present compounds or their derivatives, including prodrug forms of these agents, can be provided in the form of pharmaceutically acceptable salts. As used herein, the term pharmaceutically acceptable salts or complexes refers to appropriate salts or complexes of the active compounds according to the present invention which retain the desired biological activity of the parent compound and exhibit limited toxicological effects to normal cells. Nonlimiting examples of such salts are (a) acid addition salts formed with inorganic acids (for example, hydrochloric acid, hydrobromic acid, sulfuric acid, phosphoric acid, nitric acid, and the like), and salts formed with organic acids such as acetic acid, oxalic acid, tartaric acid, succinic acid, malic acid, ascorbic acid, benzoic acid, tannic acid, pamoic acid, alginic acid, and polyglutamic acid, among others; (b) base addition salts formed with metal cations such as zinc, calcium, sodium, potassium, and the like, among numerous others.

Modifications of the active compound can affect the solubility, bioavailability and rate of metabolism of the active species, thus providing control over the delivery of the active species. Further, the modifications can affect the anti-angiogenesis activity of the compound, in some cases increasing the activity over the parent compound. This can easily be assessed by preparing the derivative and testing its activity according to known methods well within the routineer's skill in the art.

The compounds of this invention may be incorporated into formulations for all routes of administration including for example, oral, topical and parenteral including intravenous, intramuscular, eye or ocular, intraperitoneal, intrabuccal, transdermal and in suppository form.

Pharmaceutical compositions based upon these novel chemical compounds comprise the above-described compounds in a therapeutically effective amount for treating neoplasia, cancer and other diseases and conditions which have been described herein, including psoriasis, venous ulcers, acne, rosacea, warts, eczema, hemangiomas, lymphangiogenesis and chronic inflammatory diseases, including arthritis, among others, optionally in combination with a pharmaceutically acceptable additive, carrier and/or excipient. One of ordinary skill in the art will recognize that a therapeutically effective amount of one of more compounds according to the present invention will vary with the infection or condition to be treated, its severity, the treatment regimen to be employed, the pharmacokinetics of the agent used, as well as the patient (animal or human) treated.

In the pharmaceutical aspect according to the present invention, the compound according to the present invention is formulated preferably in admixture with a pharmaceutically acceptable carrier, excipient or additive. In general, it is preferable to administer the pharmaceutical composition in orally-administrable form, but for treatment of a number of conditions, a number of other formulations may be administered via a topical, parenteral, intravenous, intramuscular, transdermal, buccal, subcutaneous, suppository or other route, including an eye or ocular route. Intravenous and intramuscular formulations are preferably administered in sterile saline. Of course, one of ordinary skill in the art may modify the formulations within the teachings of the specification to provide numerous formulations for a particular route of administration without rendering the compositions of the present invention unstable or compromising their therapeutic activity. In particular, the modification of the present compounds to render them more soluble in water or other vehicle, for example, may be easily accomplished by minor modifications (salt formulation, esterification, etc.) which are well within the ordinary skill in the art. It is also well within the routineer's skill to modify the route of administration and dosage regimen of a particular compound in order to manage the pharmacokinetics of the present compounds for maximum beneficial effect to the patient.

In certain pharmaceceutical dosage forms, the pro-drug form of the compounds may be preferred. One of ordinary skill in the art will recognize how to readily modify the present compounds to pro-drug forms to facilitate delivery of active compounds to a targeted site within the host organism or patient. The routineer also will take advantage of favorable pharmacokinetic parameters of the pro-drug forms, where applicable, in delivering the present compounds to a targeted site within the host organism or patient to maximize the intended effect of the compound.

Pharmaceutically acceptable salt forms may be the preferred chemical form of compounds according to the present invention for inclusion in pharmaceutical compositions according to the present invention.

The amount of compound included within therapeutically active formulations according to the present invention is an effective amount for treating the infection or condition. In general, a therapeutically effective amount of the present preferred compound in dosage form usually ranges from slightly less than about 0.025 mg/kg to about 2.5 g/kg, preferably about 2.5–5 mg/kg to about 100 mg/kg of the patient or considerably more, depending upon the compound used, the condition or infection treated and the route of administration, although exceptions to this dosage range may be contemplated by the present invention. In its most preferred form, compounds according to the present invention are administered in amounts ranging from about 1 mg/kg to about 100 mg/kg. Where drug delivery is systemic rather than topical, this dosage range generally produces effective blood level concentrations of active compound ranging from less than about 0.04 to about 400 micrograms/cc or more of blood in the patient.

Administration of the active compound may range from continuous (intravenous drip) to several oral administrations per day (for example, Q.I.D.) and may include oral, topical, eye or ocular, parenteral, intramuscular, intravenous, subcutaneous, transdermal (which may include a penetration enhancement agent), buccal and suppository administration, among other routes of administration, including through an eye or ocular route.

To prepare the pharmaceutical compositions according to the present invention, a therapeutically effective amount of one or more of the compounds according to the present invention is preferably intimately admixed with a pharmaceutically acceptable carrier according to conventional pharmaceutical compounding techniques to produce a dose. A carrier may take a wide variety of forms depending on the form of preparation desired for administration, e.g., oral, topical or parenteral, including gels, creams ointments, lotions and time released implantable preparations, among numerous others. In preparing pharmaceutical compositions in oral dosage form, any of the usual pharmaceutical media may be used. Thus, for liquid oral preparations such as suspensions, elixirs and solutions, suitable carriers and additives including water, glycols, oils, alcohols, flavouring agents, preservatives, colouring agents and the like may be used. For solid oral preparations such as powders, tablets, capsules, and for solid preparations such as suppositories, suitable carriers and additives including starches, sugar carriers, such as dextrose, mannitol, lactose and related carriers, diluents, granulating agents, lubricants, binders, disintegrating agents and the like may be used. If desired, the tablets or capsules may be enteric-coated or sustained release by standard techniques.

For parenteral formulations, the carrier will usually comprise sterile water or aqueous sodium chloride solution, though other ingredients including those which aid dispersion may be included. Of course, where sterile water is to be used and maintained as sterile, the compositions and carriers must also be sterilized. Injectable suspensions may also be prepared, in which case appropriate liquid carriers, suspending agents and the like may be employed.

The present compounds may be used to treat animals, and in particular, mammals, including humans, as patients. Thus, humans and other animals, and in particular, mammals, suffering from tumors, and in particular, cancer, or other diseases as disclosed herein, can be treated by administering to the patient an effective amount of one or more of the compounds according to the present invention or its derivative or a pharmaceutically acceptable salt thereof optionally in a pharmaceutically acceptable carrier or diluent, either alone, or in combination with other known pharmaceutical agents (depending upon the disease to be treated). Treatment according to the present invention can also be administered in conjunction with other conventional cancer therapies, such as radiation treatment or surgery.

The active compound is included in the pharmaceutically acceptable carrier or diluent in an amount sufficient to deliver to a patient a therapeutically effective amount for the desired indication, without causing serious toxic effects in the patient treated.

The compound is conveniently administered in any suitable unit dosage form, including but not limited to one containing 1 to 3000 mg, preferably 5 to 500 mg of active ingredient per unit dosage form. An oral dosage of 10–250 mg is usually convenient.

The concentration of active compound in the drug composition will depend on absorption, distribution, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

Oral compositions will generally include an inert diluent or an edible carrier. They may be enclosed in gelatin capsules or compressed into tablets. For the purpose of oral therapeutic administration, the active compound or its pro-drug derivative can be incorporated with excipients and used in the form of tablets, troches, or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a dispersing agent such as alginic acid or corn starch; a lubricant such as magnesium stearate; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material-of the above type, a liquid carrier such as a fatty oil. In addition, dosage unit forms can contain various other materials which modify the physical form of the dosage unit, for example, coatings of sugar, shellac, or enteric agents.

The active compound or pharmaceutically acceptable salt thereof may also be administered as a component of an elixir, suspension, syrup, wafer, chewing gum or the like. A syrup may contain, in addition to the active compounds, sucrose or fructose as a sweetening agent and certain preservatives, dyes and colorings and flavors.

The active compound or pharmaceutically acceptable salts thereof can also be mixed with other active materials that do not impair the desired action, or with materials that supplement the desired action, such as other anticancer agents, and in certain instances depending upon the desired therapy or target, antibiotics, antifungals, antiinflammatories, antiviral compounds or other agents having a distinct pharmacological effect.

Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic. If administered intravenously, preferred carriers include, for example, physiological saline or phosphate buffered saline (PBS).

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art.

Liposomal suspensions may also be pharmaceutically acceptable carriers. These may be prepared according to methods known to those skilled in the art. For example, liposomal formulations may be prepared by dissolving appropriate lipid(s) in an inorganic solvent that is then evaporated, leaving behind a thin film of dried lipid on the surface of the container. An aqueous solution of the active compound are then introduced into the container. The container is then swirled by hand to free lipid material from the sides of the container and to disperse lipid aggregates, thereby forming the liposomal suspension. Other methods of preparation well known by those of ordinary skill may also be used in this aspect of the present invention.

Numerous biological assays have been used and are accepted by those skilled in the art to assess the anti-tumor and anti-cancer activity of compounds according to the present invention. Any of these methods can be used to evaluate the activity of the compounds disclosed herein.

One common method of assessing activity is through the use of test panels of cancer cell lines. These tests evaluate the in vitro anti-cancer activity of particular compounds in cancer cell lines, and provide predictive data with respect to the use of tested compounds in vivo. Other assays include in vivo evaluations of the compound's effect on human or in an appropriate animal model, for example, using mouse tumor cells implanted into or grafted onto mice or in other appropriate animal models.

In the case of testing the anti-angiogenic/anti-cancer activity of compounds according to the present invention, an assay based on SVR cells may be employed. See, for example, Arbiser, et al., *J. Am. Acad. Derm.*, pp. 925–929 (June, 1999). In this assay, SVR cells, which are derived from primary murine endothelial cellsa by the sequential introduction of SV40 large T antigen and activated H-ras according to the method of Arbiser, et al., *Proc. Natl. Acad. Sci. USA* 1997, 94:861–6, are seeded onto a 24 well dish and treated with a compound according to the present invention at known concentration. The cell numbers are counted and compared against controls. Percent inhibition is readily determined from the data obtained. Other methods, well-known in the art, may also be used.

Chemical Synthesis

Most of the compounds according to the present invention are synthesized using well-known methods of the art. For example, chalcone compounds which are based upon a chemical structure where Q and/or T are phenyl-substituted derivatives and V is propenone (e.g. chalcone, etc., see FIG. 1) are prepared by condensing an aldehyde and ketone followed by dehydration (loss of $H_2O$ to form a double bond) to form an enone moiety. In this aspect of the present invention, the corresponding substituted benzaldehyde and the corresponding substituted acetophenone compounds are mixed in a reaction vessel or flask and the reactants are then stirred in the presence of base (e.g., about 40% NaOH) at a temperature reflective of the reaction conditions. After a period of time (generally, several hours or more, depending upon reactivity of the starting materials), the solution is filtered or extracted with chloroform or other hydrophobic solvent. The solid is recrystallized, generally from ethanol. The chloroform extracts (from above) are dried with magnesium sulfate and are evaporated at reduced pressure. Column chromatography using silical gel provides the pure chalcone derivative.

Provided infra, are a number of general synthetic methods for affording chalcone derivatives according to the present invention. It is important to note that the synthesized disclosed herein are general syntheses, and one of ordinary skill may readily determine or provide alternative syntheses for producing compounds according to the present invention without engaging in undue experimentation.

In the following descriptions, a general synthetic method is provided for each of the disclosed groups of chemical compounds. One of ordinary skill will recognize to substitute appropriately modified starting materials containing the various substituents as set forth hereinbelow. One of ordinary skill will readily synthesize the disclosed compounds according to the present invention using conventional synthetic organic techniques from starting materials which are either purchased or may be readily prepared using prior art methods.

Using the general and specific synthetic methodologies described hereinbelow, we have synthesized a number of the chemical compounds as set forth in Tables 1–6. Note that the chalcone compounds set forth in Table 2, attached, were purchased prior to testing.

Having generally described the invention, reference is now made to the following general and specific examples which are intended to illustrate preferred and other embodiments of and comparisons with the present invention. The included examples are not to be construed as limiting the scope of this invention as is more broadly set forth above and in the appended claims.

In the following disclosure, general synthetic methods are set forth for all compounds according to the present invention, including, for example, propenone derivatives, cyclohexenone and cyclopentanone derivatives, indandione derivatives, tetralone derivatives, propynone derivatives, acetophenone derivatives, benzylidene acetone derivatives, alkanone and cycloalkanone derivatives, camphor derivatives, stilbene derivatives, naphthylene derivatives, alkanedione derivatives, pyridine derivatives, among numerous other compounds. In addition, disclosure related to experimentals which resulted in specific compounds according to the present invention is also presented.

I. Propenone Derivatives

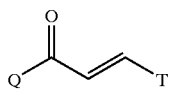

where Q and T are independently selected from

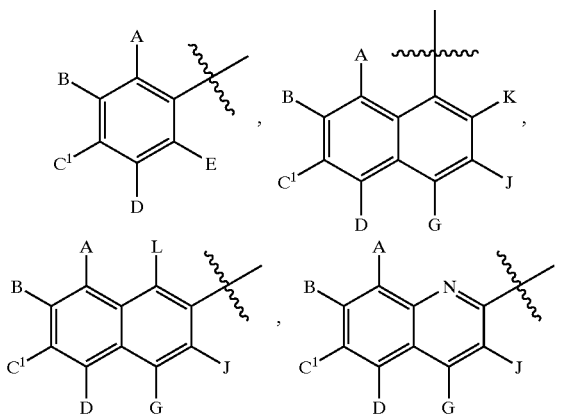

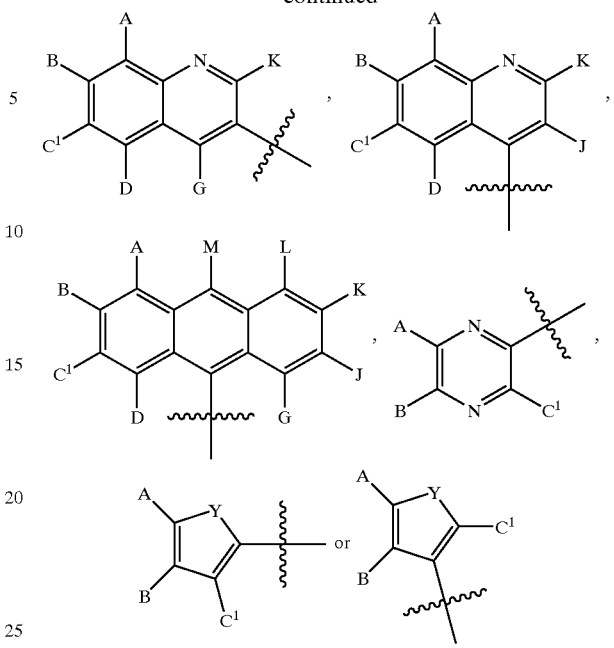

where A, B, C$^1$, D, E, G, J, K, L and M are independently selected from H, a C$_1$–C$_3$ alkyl group, a halogen, an OR$_1$ group, COOH, COOR$_1$, an alkylene ester group according to the structure —(CH$_2$)$_m$COOR$_1$ or a CF$_3$ group.

where subscript m is any integer.

where Y is O, S, N—H, N—CH$_3$, N—CH$_2$CH$_3$ or CH$_2$.

where R$_1$ is a C$_1$–C$_4$ alkyl group.

To a 0.67 M solution of the benzaldehyde (10 mmol) and the acetophenone (10 mmol) in ethanol (15 ml) is added 10 ml of 40% NaOH at 10° C. After stirring overnight at room temperature, the solution is filtered. The precipitate is recrystallized from the appropiate solvent (usually ethanol) to afford the pure product.

II. 3,6-DIPHENYL-2-CYCLOHEXENONE Derivatives

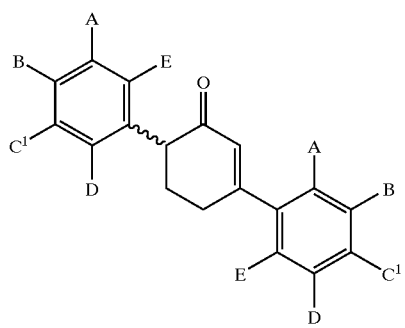

where A, B, C$^1$, D and E are independently selected from H, a C$_1$–C$_3$ alkyl group, a halogen, an OR$_1$ group, COOH, COOR$_1$, an alkylene ester group according to the structure —(CH$_2$)$_m$COOR$_1$ or a CF$_3$ group.

where subscript m is any integer.

where R$_1$ is a C$_1$–C$_4$ alkyl group.

The 3-chloropropiophenone (7.45 mmol) and the phenylacetone (7.45 mmol) were placed in a round-bottom flask and stirred while 5 N KOH in MeOH is added dropwise to the solution. After stirring for 12 hours, the reaction is neutralized with 50% HCl, and the aqueous layer is extracted with ether. The ether extracts were washed with water, dried with MgSO$_4$, and evaporated to yield the crude product, which is chromatographed on silica gel to afford the pure product.

III. Indandione Derivatives

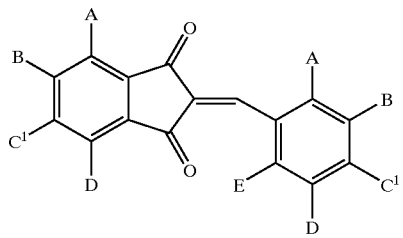

where A, B, C$^1$, D and E are independently selected from H, a C$_1$–C$_3$ alkyl group, a halogen, an OR$_1$ group, COOH, COOR$_1$, an alkylene ester group according to the structure —(CH$_2$)$_m$COOR$_1$ or a CF$_3$ group.

where subscript m is any integer.

where R$_1$ is a C$_1$–C$_4$ alkyl group.

Boron oxide (10.26 mmol) and the benzaldehyde (7.53 mmol) were added to a stirred solution of the indandione (6.84 mmol), piperidine (3 drops), and benzene (0.67 M). The solution is refluxed with stirring for 30 minutes. After filtration of the solution, the filtrate is concentrated under reduced pressure. The resulting crystalline solid is recrystallized from ethanol. If no solid formed, a standard ether work-up followed by column chromatography on silica gel purified the product.

IV. Tetralone Derivatives

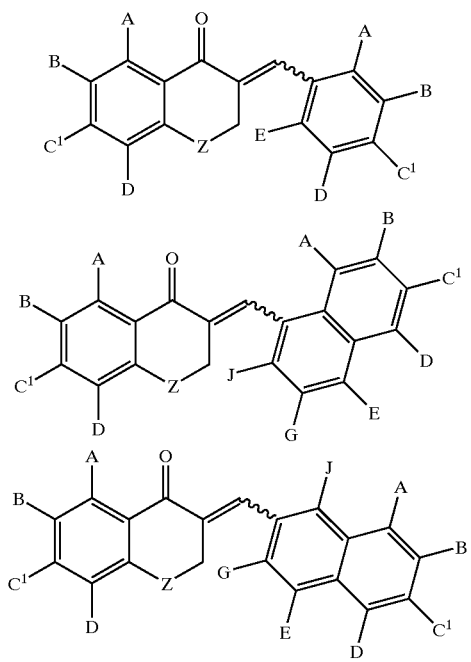

where A, B, C$^1$, D, E, G and J are independently selected from H, a C$_1$–C$_3$ alkyl group, a halogen, an OR$_1$ group, COOH, COOR$_1$, an alkylene ester group according to the structure —(CH$_2$)$_m$COOR$_1$ or a CF$_3$ group.

where subscript m is any integer.

where Z is O, S, N—H, N—CH$_2$, N—CH$_2$CH$_3$ or CH$_2$.

where R$_1$ is a C$_1$–C$_4$ alkyl group.

To a 0.67 M solution of the benzaldehyde (10 mmol) and the tetralone (10 mmol) in ethanol (15 ml) is added 10 ml of 40% NaOH at 10° C. After stirring overnight at room temperature, the solution is filtered. The precipitate is recrystallized from the appropiate solvent (usually ethanol) to afford the pure product V. Propynone Derivatives

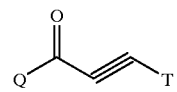

where Q and T are independently selected from

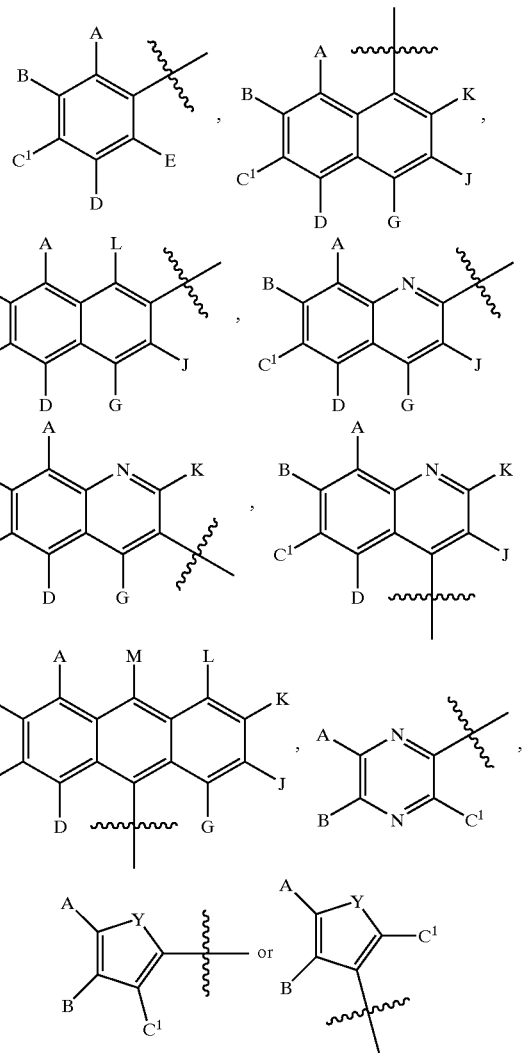

where A, B, C$^1$, D, E, G, J, K, L and M are independently selected from H, a C$_1$–C$_3$ alkyl group, a halogen, an OR$_1$ group, COOH, COOR$_1$, an alkylene ester group according to the structure —(CH$_2$)$_m$COOR$_1$ or a CF$_3$ group.

where subscript m is any integer.

where Y is O, S, N—H, N—CH$_3$, N—CH$_2$CH$_3$ or CH$_2$.

where R$_1$ is a C$_1$–C$_4$ alkyl group.

To the stirred 0.45 M solution of the propenone (4.80 mmol) in chloroform (10.7 mL) at 0° C. is added dropwise a 0.6 M solution of bromine (4.90 mmol) in CHCl$_3$(8.2 mL) over 30 minutes. The solution is stirred for 2 hrs at room temperature. The solvent is evaporated to yield the crude product, which is recrystallized from ethanol. If the product is not a solid, a standard ether work-up followed by column chromatography on silica gel yielded the 2,3-dibromopropanone derivatives.

Sodium bicarbonate (3.26 mmol) is added to a solution of the 2,3-dibromopropanone (2.72 mmol) in 4 ml 95% ethanol (0.68 M). The solution is stirred and refluxed for 2 hours (TLC is used to determine the end of the reaction.). The solvent is evaporated, and the crude product is diluted in ether. The precipitate (NaBr) is filtered. The ether layer is washed with water, dried with $MgSO_4$, and evaporated to yield the crude product. Chromatography on silica gel yielded the alpha-bromopropenone derivative.

Potassium hydroxide (3.48 mmol), dissolved in water (0.87 M (4.0 ml)), is added over about 30 minutes to a refluxing solution of the alpha-bromochalcone (3.48 mmol) in 0.35 M of 1:1 water/acetone (5 ml each). After 20 minutes of further refluxing, the solution is cooled and diluted with water. The water is extracted with ether, which is dried with $MgSO_4$ and evaporated. Chromatography on silica gel yielded 1,3-diphenylpropynone and its derivatives.

VI. alpha-Tetralonylideneacetophenone Derivatives

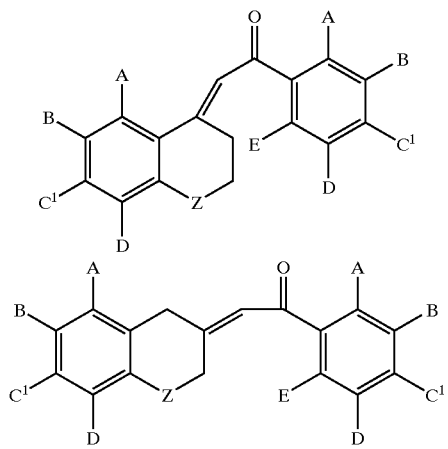

where A, B, $C^1$, D and E are independently selected from H, a $C_1$–$C_3$ alkyl group, a halogen, an $OR_1$ group, COOH, $COOR_1$, an alkylene ester group according to the structure —$(CH_2)_m COOR_1$ or a $CF_3$ group.

where subscript m is any integer.

where Z is O, S, N—H, N—$CH_3$, N—$CH_2CH_3$ or $CH_2$.

where $R_1$ is a $C_1$–$C_4$ alkyl group.

To a stirred 0.2 M solution of the derivatized tetralone (1.71 mmol) in acetonitrile (8.55 ml) is added benzoylmethylene triphenylphosphorane (2.57 mmol). The mixture is stirred and refluxed for several hours (TLC determined the end of the reaction). The solution is concentrated by evaporation to afford the crude product, which is purified with column chromatography on silica gel.

VII. 2,6-DIBENZYLIDENECYCLOHEXANONE Derivatives

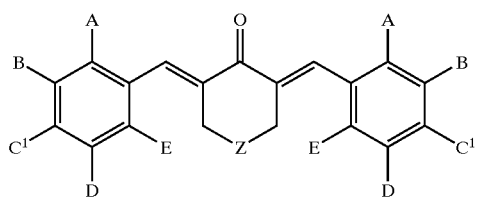

where A, B, $C^1$, D and E are independently selected from H, a $C_1$–$C_3$ alkyl group, a halogen, an $OR_1$ group, COOH, $COOR_1$, an alkylene ester group according to the structure —$(CH_2)_m COOR_1$ or a $CF_3$ group.

where subscript m is any integer.

where Z is O, S, N—H, N—$CH_3$, N—$CH_2CH_3$ or $CH_2$.

where $R_1$ is a $C_1$–$C_4$ alkyl group.

To a 0.67 M solution of the benzaldehyde (20.0 mmol) and cyclohexanone (10.0 mmol) in ethanol (15 ml) is added 10 ml 40% KOH at 10° C. After stirring for 12–24 hr at room temperature, the solution is diluted and filtered. The precipitate is recrystallized from ethanol to afford 2,6-dibenzalcyclohexanone and its derivatives.

VIII. 2,6-DIBENZYLIDENECYCLOPENTANONE Derivatives

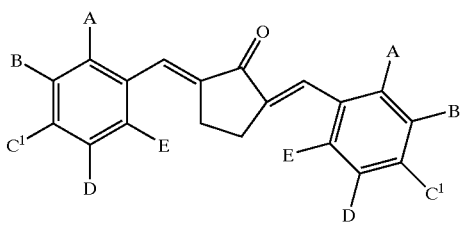

where A, B, $C^1$, D and E are independently selected from H, a $C_1$–$C_3$ alkyl group, a halogen, an $OR_1$ group, COOH, $COOR_1$, an alkylene ester group according to the structure —$(CH_2)_m COOR_1$ or a $CF_3$ group.

where subscript m is any integer.

where $R_1$ is a $C_1$–$C_4$ alkyl group.

To a 0.67 M solution of the benzaldehyde (20.0 mmol) and cyclopentanone (10.0 mmol) in ethanol (15 ml) is added 10 ml 40% KOH at 10° C. After stirring for 12–24 hr at room temperature, the solution is diluted and filtered. The precipitate is recrystallized from ethanol to afford 2,6-dibenzalcyclopentanone and its derivatives.

IX. Benzylideneacetone Derivatives

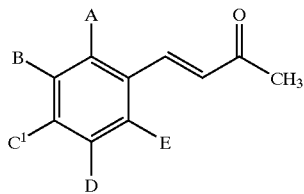

where A, B, $C^1$, D and E are independently selected from H, a $C_1$–$C_3$ alkyl group, a halogen, an $OR_1$ group, COOH, $COOR_1$, an alkylene ester group according to the structure —$(CH_2)_m COOR_1$ or a $CF_3$ group.

where subscript m is any integer.

where $R_1$ is a $C_1$–$C_4$ alkyl group.

To a stirred solution of the benzaldehyde (8.00 mmol) and of acetone (22 mmol) in a 25-ml erlenmeyer flask in an ice bath is added dropwise 0.2 ml of a 10% NaOH solution. The temperature is not allowed to exceed 30° C. during the addition and is stirred for an additional 2 hours at room temperature after the addition. The reaction is quenched with dilute HCl until the solution became slightly acidic. The aqueous layer is extracted with toluene, and the combined organic extracts were washed with water and dried with $MgSO_4$. The toluene is removed by fractional distillation at atmospheric pressure, and the pure product is collected from distillation at reduced pressure or by column chromatography on silica gel.

X. 2-BENZYLIDENECYCLOALKANONE Derivatives

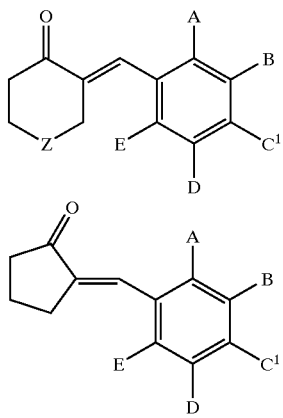

where A, B, $C^1$, D and E are independently selected from H, a $C_1$–$C_3$ alkyl group, a halogen, an $OR_1$ group, COOH, $COOR_1$, an alkylene ester group according to the structure —$(CH_2)_m COOR_1$ or a $CF_3$ group.

where subscript m is any integer.

where Z is O, S, N—H, N—$CH_3$, N—$CH_2CH_3$ or $CH_2$.

where $R_1$ is a $C_1$–$C_4$ alkyl group.

To a stirred solution of the benzaldehyde (3.64 mmol) and the cycloalkanone derivative (10.0 mmol) in a 25-ml erlenmeyer flask in an ice bath is added dropwise 0.1 ml of a 10% NaOH solution. The mixture is not allowed to exceed 30° C. during the addition and is stirred for an additional 2 hours at room temperature after the addition. The reaction is quenched with dilute HCl until the solution became slightly acidic. The aqueous layer is extracted with chloroform, and the combined organic extracts were washed with water, dried with $MgSO_4$, and evaporated to yield the crude product. Pure product is obtained by column chromatography on silica gel.

XI. 1-CYCLOALKYLPROPENONE Derivatives

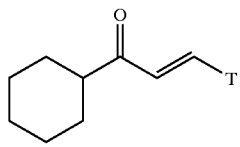

where T is independently selected from

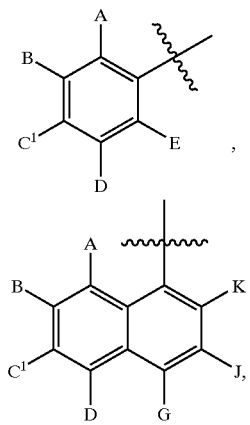

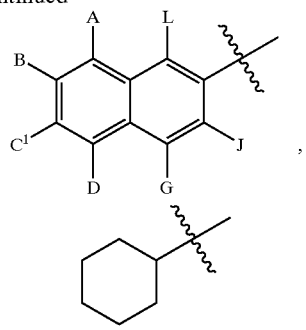

where A, B, $C^1$, D, E, G, J, K, and L are independently selected from H, a $C_1$–$C_3$ alkyl group, a halogen, an $OR_1$ group, COOH, $COOR_1$, an alkylene ester group according to the structure —$(CH_2)_m COOR_1$ or a $CF_3$ group.

where subscript m is any integer.

where $R_1$ is a $C_1$–$C_4$ alkyl group.

To a stirred 0.44 M solution of cyclohexyl methyl ketone (10 mmol) in THF at −78° C. under nitrogen is added lithium diisopropylamide (10 mmol) dropwise via syringe over 20 minutes. After 40 minutes of stirring, a specific aldehyde (12 mmol) in THF (2 M) is added dropwise via syringe over 2 to 3 minutes, and the reaction is allowed to warm slowly to room temperature. The THF is evaporated, and water is added. Standard ether work-up and column chromatography on silica gel provided the product. In order to form the dicyclohexylpropenone, the aldol product from the above reaction is refluxed in ethanol and aqueous HCl for several hours. Water is added, and a standard ether work-up followed by column chromatography on silica gel provided the pure product.

XII. 3-CYCLOALKYLPROPENONE Derivatives

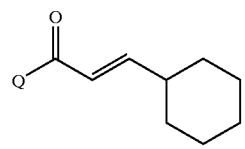

where Q is independently selected from

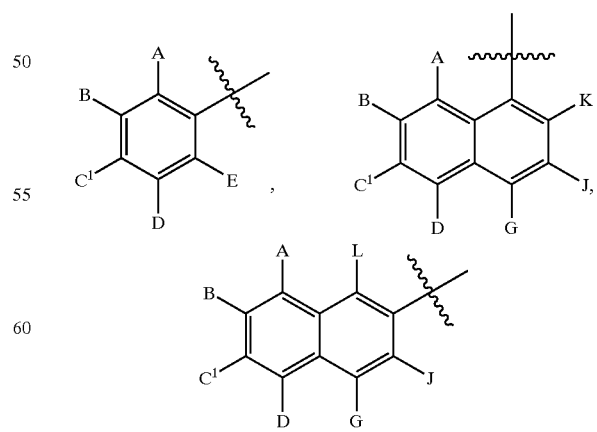

where A, B, $C^1$, D, E, G, J, K, and L are independently selected from H, a $C_1$–$C_3$ alkyl group, a halogen, an $OR_1$ group, COOH, $COOR_1$, an alkylene ester group according to the structure —$(CH_2)_mCOOR_1$ or a $CF_3$ group.

where subscript m is any integer.

where $R_1$ is a $C_1$–$C_4$ alkyl group.

NaH (60% dispersion in oil, 16.6 mmol) is added to a round-bottom flask and is rinsed with hexane three times to remove the oil. The flask is put in an ice bath, and the NaH is put under a nitrogen atmosphere. A 0.4 M solution of aryl methyl ketone (10 mmol) in THF is added dropwise via syringe over several minutes. After 10 minutes of stirring at room temperature, cyclohexanecarboxaldehyde (12 mmol) in TRF (2 M) is added dropwise via syringe over 2 to 3 minutes. Stirring is continued overnight. The THF is evaporated, and water is added. Standard ether work-up and column chromatography provided the product.

XIII. Camphor Derivatives

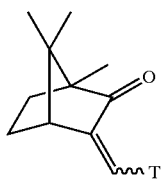

where T is independently selected from

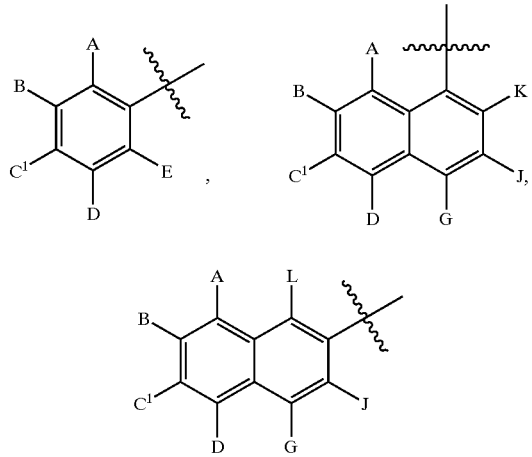

where A, B, $C^1$, D, E, G, J, K, and L are independently selected from H, a $C_1$–$C_3$ alkyl group, a halogen, an $OR_1$ group, COOH, $COOR_1$, an alkylene ester group according to the structure —$(CH_2)_mCOOR_1$ or a $CF_3$ group.

where subscript m is any integer.

where $R_1$ is a $C_1$–$C_4$ alkyl group.

NaH (60% dispersion in oil, 16.6 mmol) is added to a round-bottom flask and is rinsed with hexane three times to remove the oil. The flask is put in an ice bath, and the NaH is put under a nitrogen atmosphere. A 0.4 M solution of camphor (10 mmol) in THF is added dropwise via syringe over several minutes. After 10 minutes of stirring at room temperature, the appropriate aldehyde (12 mmol) in THF (2 M) is added dropwise via syringe over 2 to 3 minutes. Stirring is continued overnight. The THF is evaporated, and water is added. Standard ether work-up and column chromatography using silica gel provided the product.

XIV. Stilbene Derivatives

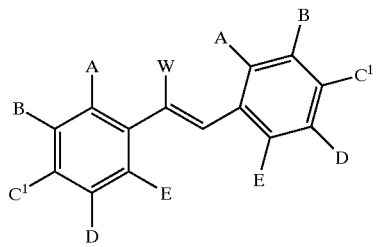

where A, B, $C^1$, D, E, G, J, K, and L are independently selected from H, a $C_1$–$C_3$ alkyl group, a halogen, an $OR_1$ group, COOH, $COOR_1$, an alkylene ester group according to the structure —$(CH_2)_mCOOR_1$ or a $CF_3$ group.

where subscript m is any integer.

where W is chosen from $COOR_1$, $COR_1$, CN, and COPh.

where $R_1$ is a $C_1$–$C_4$ alkyl group.

To a 0.67 M solution of the functionalized benzaldehyde (10 mmol) and the benzyl ketone, ester, or nitrile (10 mmol) in ethanol (15 ml) is added 10 ml of 40% NaOH at 10° C. After stirring overnight at room temperature, the solution is filtered. The precipitate is recrystallized from the appropiate solvent (usually ethanol) to afford the pure product

XV. Benzoyldihydronaphthylene Derivatives

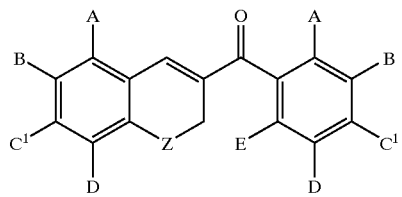

where A, B, $C^1$, D, and E are independently selected from H, a $C_1$–$C_3$ alkyl group, a halogen, an $OR_1$ group, COOH, $COOR_1$, an alkylene ester group according to the structure —$(CH_2)_mCOOR_1$ or a $CF_3$ group.

where subscript m is any integer.

where Z is O, S, N—H, N—$CH_3$, N—$CH_2CH_3$ or $CH_2$.

where $R_1$ is a $C_1$–$C_4$ alkyl group.

To a stirred solution of the carbonyl chloride (5 mmol) in THF (0.4 M) in an ice bath is added phenylmagnesium bromide (5 mmol) in THF (1 M) dropwise over several minutes. After addition, the solution stirred overnight at room temperature. The THF is evaporated, and water is added. A standard ether work-up followed by column chromatography on silica gel provided the pure product.

XVI. 2-BENZYLIDENEALKANEDIONE Derivatives

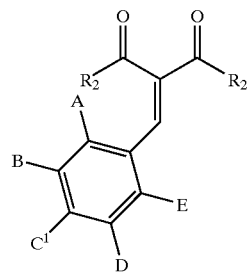

where A, B, $C^1$, D and E are independently selected from H, a $C_1$–$C_3$ alkyl group, a halogen, an $OR_1$ group, COOH, COOR$_1$, an alkylene ester group according to the structure —(CH$_2$)$_m$COOR$_1$ or a CF$_3$ group.

where subscript m is any integer.

where R$_1$ is a C$_1$–C$_4$ alkyl group.

where R$_2$ is a C$_1$–C$_4$ alkyl group or a phenyl group.

To a 0.67 M solution of the benzaldehyde (10 mmol) and the diketone (10 mmol) in ethanol (15 ml) is added 10 ml of 40% NaOH at 10° C. After stirring overnight at room temperature, the solution is filtered. The precipitate is recrystallized from the appropriate solvent (usually ethanol) to afford the pure product.

XVII. 2,6-DIBENZHYDRYLIDENECYCLOPENTANONE Derivatives

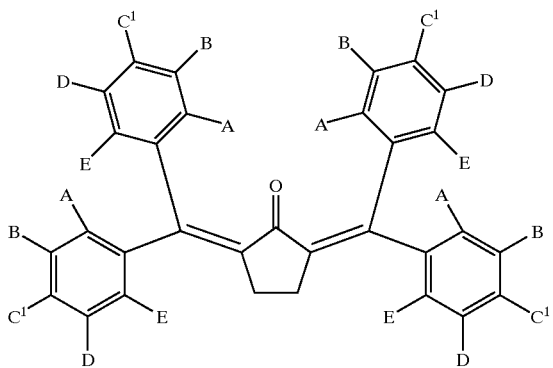

where A, B, C$^1$, D and E are independently selected from H, a C$_1$–C$_3$ alkyl group, a halogen, an OR$_1$ group, COOH, COOR$_1$, an alkylene ester group according to the structure —(CH$_2$)$_m$COOR$_1$ or a CF$_3$ group.

where subscript m is any integer.

where R$_1$ is a C$_1$–C$_4$ alkyl group.

To a 0.5 M solution of the benzophenone (20 mmol) and cyclopentanone (10 mmol) in 2-propanol (40 ml) is added 10 ml of 40% KOH at 10° C. After stirring overnight at room temperature, the solution is filtered. The precipitate is recrystallized from the appropriate solvent (usually 2-propanol) to afford the pure product.

XVIII. 2,6-DIBENZHYDRYLIDENECYCLOALKANONE Derivatives

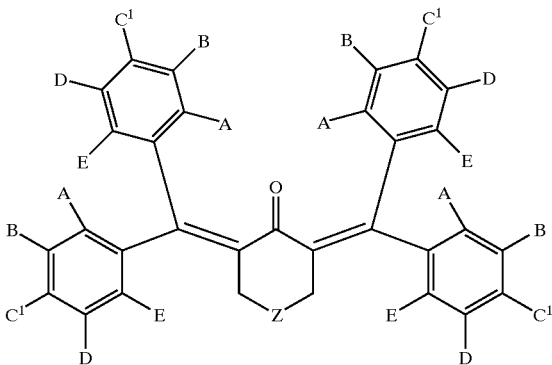

where A, B, C$^1$, D, and E are independently selected from H, a C$_1$–C$_3$ alkyl group, a halogen, an OR$_1$ group, COOH, COOR$_1$, an alkylene ester group according to the structure —(CH$_2$)$_m$COOR$_1$ or a CF$_3$ group.

where subscript m is any integer.

where Z is O, S, N—H, N—CH$_3$, N—CH$_2$CH$_3$ or CH$_2$.

where R$_1$ is a C$_1$–C$_4$ alkyl group.

To a 0.5 M solution of the benzophenone (20 mmol) and cycloalkanone (10 mmol) in 2-propanol (40 ml) is added 10 ml of 40% KOH at 10° C. After stirring overnight at room temperature, the solution is filtered. The precipitate is recrystallized from the appropriate solvent (usually 2-propanol) to afford the pure product.

XIX. 2-BENZHYDRYLIDENEALKANEDIONE Derivatives

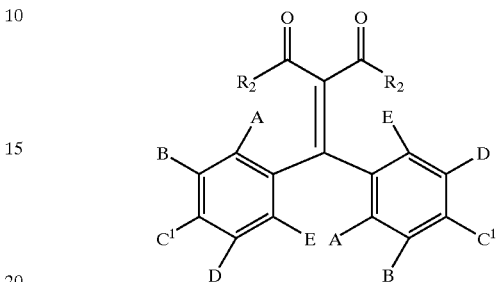

where A, B, C$^1$, D, and E are independently selected from H, a C$_1$–C$_3$ alkyl group, a halogen, an OR$_1$ group, COOH, COOR$_1$, an alkylene ester group according to the structure —(CH$_2$)$_m$COOR$_1$ or a CF$_3$ group.

where subscript m is any integer.

where R$_1$ is a C$_1$–C$_4$ alkyl group.

where R$_2$ is C$_1$–C$_4$ alkyl group or a phenyl group.

To a 0.5 M solution of the benzophenone (10 mmol) and cycloalkanedione (10 mmol) in 2-propanol (20 ml) is added 10 ml of 40% KOH at 10° C. After stirring overnight at room temperature, the solution is filtered. The precipitate is recrystallized from the appropriate solvent (usually 2-propanol) to afford the pure product.

XX. 2-BENZHYDRYLIDENEINDANDIONE Derivatives

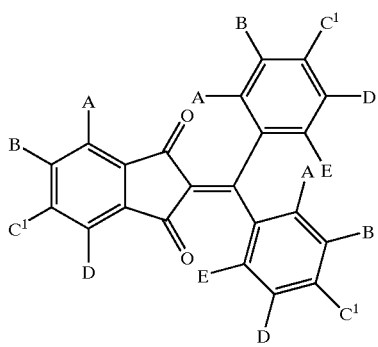

where A, B, C$^1$, D and E are independently selected from H, a C$_1$–C$_3$ alkyl group, a halogen, an OR$_1$ group, COOH, COOR$_1$, an alkylene ester group according to the structure —(CH$_2$)$_m$COOR$_1$ or a CF$_3$ group.

where subscript m is any integer.

where R$_1$ is a C$_1$–C$_4$ alkyl group.

Boron oxide (10.26 mmol) and the benzophenone (7.53 mmol) were added to a stirred solution of the indandione (6.84 mmol), piperidine (3 drops), and benzene (0.67 M). The solution is refluxed with stirring for several hours. After filtration of the solution, the filtrate is concentrated under reduced pressure. The resulting crystalline solid is recrystallized from ethanol. If no solid formed, a standard ether work-up followed by column chromatography on silica gel purified the product.

XXI. 2-BENZHYDRYLIDENECAMPHOR Derivative

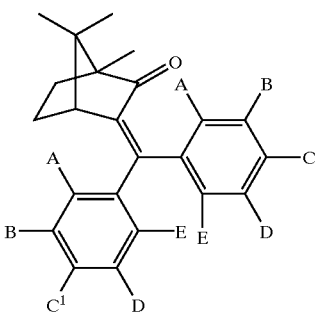

where A, B, $C^1$, D and E are independently selected from H, a $C_1$–$C_3$ alkyl group, a halogen, an $OR_1$ group, COOH, $COOR_1$, an alkylene ester group according to the structure —$(CH_2)_m COOR_1$ or a $CF_3$ group.

where subscript m is any integer.

where $R_1$ is a $C_1$–$C_4$ alkyl group.

A solution of n-BuLi (6.57 mmol) is added dropwise over several minutes to a 0.4 M suspension of camphor (6.57 mmol) in dry THF under nitrogen at 0° C. After stirring for at least 5 minutes, a 2 M solution of the benzophenone (7.23 mmol) in dry THF is added. Stirring is continued for 15 min at 0 to 5° C. and then for 1.5 hr. at room temperature, followed by removal of most of the THF by rotary evaporation. Water is added and is extracted with ether. The extracts were washed with water, dried over $MgSO_4$, and evaporated to give the crude product. Chromatography using silica gel gave the pure product.

XXII. 2-BENZHYDRYLIDENECYCLOALKANONE Derivatives

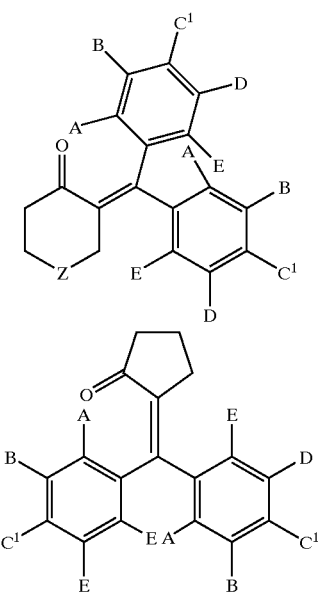

where A, B, $C^1$, D, and E are independently selected from H, a $C_1$–$C_3$ alkyl group, a halogen, an $OR_1$ group, COOH, $COOR_1$, an alkylene ester group according to the structure —$(CH_2)_m COOR_1$ or a $CF_3$ group.

where subscript m is any integer.

where Z is O, S, N—H, N—$CH_3$, N—$CH_2CH_3$ or $CH_2$.

where $R_1$ is a $C_1$–$C_4$ alkyl group.

To a stirred solution of the benzophenone (3.64 mmol) and the cycloalkanone derivative (10.0 mmol) in a 25-ml erlenmeyer flask in an ice bath is added dropwise 0.1 ml of a 10% NaOH solution. The mixture is not allowed to exceed 30° C. during the addition and is stirred for several additional hours at room temperature after the addition. The reaction is quenched with dilute HCl until it rendered litmus paper slightly acidic. The aqueous layer is extracted with chloroform, and the combined organic extracts were washed with water, dried with $MgSO_4$, and evaporated to yield the crude product. Pure product is obtained by column chromatography on silica gel.

XXIII. 2,3-DIPHENYL-2-CYCLOALKENONE Derivatives

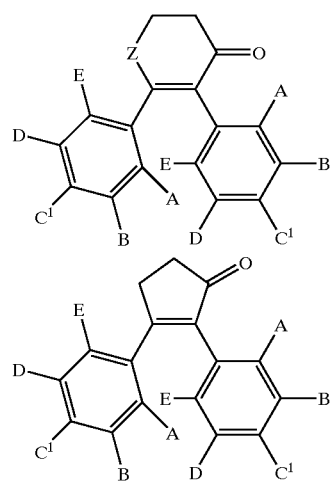

where A, B, $C^1$, D, and E are independently selected from H, a $C_1$–$C_3$ alkyl group a halogen, an $OR_1$ group, COOH, $COOR_1$, an alkylene ester group according to the structure —$(CH_2)_m COOR_1$ or a $CF_3$ group.

where subscript m is any integer.

where Z is O, S, N—H, N—$CH_3$, N—$CH_2CH_3$ or $CH_2$.

where $R_1$ is a $C_1$–$C_4$ alkyl group.

Compound 1 (2,3-Diphenyl-2-Cyclohexenone Derivatives): A solution of methyl 5-oxo-5-phenyl-2-(phenylacetyl)pentanoate (19.3 mmol) in 2% NaOH (116 ml) and 1,4-dioxane (100 ml) is refluxed for 1 hour, cooled to room temperature, evaporated in vacuo, and partitioned between chloroform and water. The chloroform extracts are washed with water, dried with $Mg_2SO_4$, and chromatographed on silica gel to yield the pure diphenylcyclohexenone derivative.

Compound 2 (2,3-Diphenyl-2-cyclopentenone Derivatives): To dibenzalacetone (9 mmol) is added 85% phosphoric acid (22.5 ml) and 90% formic acid (22.5 ml). The mixture is heated to 90° C. for 4 hours. Water (30 ml) is added and the solution is extracted with 150 ml of diethyl ether. The extracts are washed with saturated sodium bicarbonate and water, dried with $Mg_2SO_4$, and evaporated to yield crude product. Column chromatography with silica gel provides pure product.

SPECIFIC EXAMPLES

Materials and Methods. $^1$H NMR (p.m.r.) spectra were recorded on a Bruker 250 AMX spectrometer for 250 MHz, with $Me_4Si$ as internal standard. Chemical shifts (δ) are reported in parts per million (ppm) and signals are reported as s (singlet), d (doublet), t (triplet), q (quartet), m (multiplet), or br s (broad singlet). $^{13}$C NMR (c.m.r.) Are also reported in a number of instances. Reactants and solvents were generally distilled before use.

Numerous chalcone compounds were synthesized and tested to determine their potential as pharmaceutical agents. A description of the synthesis of these compounds is set forth below. The synthesis of those compounds which are not specifically described proceeds by analogy from the specific syntheses disclosed. A number of chalcone compounds, as indicated in the attached Table 2, were purchased (Aldrich Chemical Co. or Lancaster Chemical Co.) rather than synthesized before testing. Tables 1–6 indicate the compounds which were synthesized or purchased and generally tested to determine their activity as anti-angiogenesis agents.

2,3-Dibromo-1,3-diphenylpropenone. To a stirred solution of (3.00 g, 14.4 mmol) chalcone in 53.4 ml chloroform at 0° C. was added dropwise a solution of (2.35 g, 14.7 mmol) bromine in 40.8 ml of chloroform over 30 minutes. The solution was stirred for 2 hrs at room temperature. The solvent was evaporated to yield the crude product, which was recrystallized from ethanol affording 5.05 g (95.3%) of a white, flaky powder. $^1$H NMR (250 MHz) δ 8.14–8.11 (m, 2 H), 7.71–7.37 (m, 8 H), 5.88–5.84 (d, 2 H), 5.69–5.65 (d, 2 H); $^{13}$C NMR (62.7 MHz) 191.4, 138.5, 134.4, 129.6, 129.3, 129.1, 128.6, 50.0, 47.1 ppm.

α-Bromo-Z-chalcone. (41) Cromwell, *J. Am. Chem. Soc.*, 1940, 62, 2897–2900. Sodium acetate (245 mg, 2.99 mmol) was added to a solution of 2,3-dibromo-1,3-diphenyl-1-propanone (1.00 g, 2.72 mmol) in 4 ml 95% ethanol. The solution was stirred and refluxed for 2 hours. The solvent was evaporated, and the crude product was diluted in ether. The precipitate (sodium bromide) was filtered. The ether layer was washed with water, dried with magnesium sulfate, and evaporated to yield the crude product. Chromatographing twice on a column with silica gel in 9:1 hexanes:ether solvent gave 416 mg (53.3%) of the product as a yellowish-orange oil. See, Hassner, et al., *J. Am. Chem. Soc.*, 1971, 93, 981–985. $^1$H NMR (250 MHz) δ 7.90–7.81 (m, 4 H), 7.71 (s, 1 H), 7.64–7.44 (m, 6 H); $^{13}$C NMR (62.7 MHz) 191.7, 142.9, 136.7, 133.8, 132.8, 130.5, 130.4, 129.9, 128.9, 122.7 ppm.

1,3-Diphenyl-1-propanone. (42) Chalcone (2.00 g, 9.60 mmol) dissolved in 24 ml of ethyl acetate was hydrogenated with 100 mg of 10% Pd/C at 55 psi for 2 hours at room temperature. The catalyst was filtered through celite, and the solvent evaporated to give the crude product, which was chromatographed on silica gel using 4:1 hexanes:ethyl acetate yielding 1.20 g (60.0%) of a white, flaky powder. $^1$H NMR (250 MHz) δ 8.00–7.97 (m, 2 H), 7.61–7.21 (m, 8 H), 3.36–3.30 (t, 2 H), 3.13–3.07 (t, 2 H); $^{13}$C NMR (62.7 MHz) 199.4, 141.5, 137.0, 133.3, 128.8, 128.6, 128.2, 126.3, 40.6 ppm.

1,3-Di(2-furyl)propenone. (43) After stirring 2 hours, a solid formed which was filtered and washed with ethanol. Recrystallization from ethanol afforded 157 mg (18.4%) of light-yellow crystals: mp 88.1–89.3° C. (lit. mp 88–89° C., Demir, et al., *Tetrahedron Asymmetry*, 1998, 9, 1035–1042). $^1$H NMR (250 MHz) Riahi, et al, *Synth. Commun.*, 1998, 28(23)4339–4344. δ 7.66–7.52 (m, 3 H), 7.31–7.28 (m, 2 H), 6.72–6.71 (d, 1 H), 6.59–6.57 (m, 1 H), 6.52–6.50 (m, 1 H); $^{13}$C NMR (62.7 MHz) 177.9, 153.8, 151.7, 146.7, 145.2, 130.0, 119.0, 117.6, 116.5, 112.9, 112.6 ppm.

1-(2-Furyl)-3-phenylpropenone. (44) After stirring 2 hours, a solid formed which was filtered and washed with ethanol. 300 mg (15.2%) of light-yellow flakes resulted: mp 88.2–89.5° C. (lit. mp 89–90° C., Shibata, et al., *J. Heterocylic Chem.*, 1991, 28, 161–165). $^1$H NMR (250 MHz) δ 7.92–7.86 (d, 1 H), 7.68–7.64 (m, 3 H), 7.49–7.39 (m, 4 H), 7.35–7.34 (d, 1 H), 6.61–6.59 (m, 1 H); $^{13}$C NMR (62.7 MHz) 178.2, 153.8, 146.7, 144.2, 134.9, 130.8, 129.1, 128.7, 121.3, 117.7, 112.7 ppm.

3-(2-Furyl)-1-phenylpropenone. (45) After stirring 4 hours, a standard chloroform workup provided the crude product. Column chromatography with silica gel using 4:1 hexanes:ethyl acetate afforded 390 mg (19.7%) of a viscous yellow oil. Shibata, et al., *J. Heterocylic Chem.*, 1991, 28, 161–165, H NMR (250 MHz) δ 8.06–8.02 (m, 2 H), 7.64–7.44 (m, 6 H), 6.74–6.73 (d, 1 H), 6.54–6.52 (m, 1 H); $^{13}$C NMR (62.7 MHz) 190.0, 151.8, 145.1, 138.4, 132.9, 130.8, 128.8, 128.6, 119.5, 116.4, 112.8 ppm.

3-(2,6-Dichlorobenzylidene)-4-chromanone. (67) To a solution of 2,6-dichloro-benzaldehyde (649 mg, 3.71 mmol) and 4-chromanone (500 mg, 3.37 mmol) in 8.4 ml of ethanol heated almost to boiling was added 1.7 ml of concentrated hydrochloric acid dropwise. After refluxing for 1 day, the solution was cooled overnight, and a precipitate formed. The precipitate was recrystallized from ethanol to afford 250 mg (25.0%) of white flakes. $^1$H NMR (250 MHz) δ 8.07–8.04 (dd, 1 H), 7.66 (s, 1 H), 7.53–7.47 (m, 1 H), 7.40–7.24 (m, 3 H), 7.11–7.06 (t, 1 H), 6.99–6.96 (d, 1 H), 4.88 (s, 2H); $^{13}$C NMR (62.7 MHz) 181.6, 161.9, 136.2, 134.9, 134.8, 132.4, 130.4, 128.4, 128.2, 122.2, 118.3, 68.3 ppm. Elemental Analysis. Calculated for $C_{16}H_{10}Cl_2O_2$: C, 62.97; H, 3.31. Found: C, 63.05; H, 3.35.

General Procedure for Enone Derivatives. The method of Maitra, et al. *Synth. Commu.*, 19(13,14), 2363–2370 (1989), as followed, with modifications. To a solution of the aldehyde (10 mmol) and the methyl ketone or cyclic ketone (10 mmol) in 15 ml of ethanol was added 10 ml of 40% potassium hydroxide in water at 10° C. After stirring for a specific amount of time at room temperature, the solution was filtered. The precipitate was recrystallized from the appropriate solvent to afford the pure product.

3-(1-Naphthyl)-1-phenylpropenone. A viscous oil formed after stirring 2 hours and was extracted with ether. After a standard ether workup, a solid formed and was recrystallized from a 9:1 ethanol:chloroform solution to give 700 mg (27.1%) of yellow platelets: mp 75.8–76.4° C. (lit. mp 76° C., Maitra, et al, supra) $^1$H NMR (250 MHz) δ 8.73–8.67 (d, 1 H), 8.29–8.26 (d, 1 H), 8.12–8.09 (d, 2 H), 7.96–7.89 (m, 3 H), 7.68–7.51 (m, 7 H); $^{13}$C NMR (62.7 MHz) 190.5, 141.9, 138.4, 133.9, 133.1, 132.5, 131.9, 131.0, 128.8, 128.3, 127.2, 126.5, 125.6, 125.3, 124.8, 123.7 ppm.

3-(2,6-Dichlorophenyl)-1-(2-naphthyl)propenone. (59) 30 ml of methanol and 2 ml of 40% sodium hydroxide in water were used. After stirring 2 hours, a solid formed and was filtered. Recrystallization from ethanol afforded 2.28 g (69.7%) of a faint-yellow powder. $^1$H NMR (250 MHz) δ 8.53 (s, 1 H), 8.14–8.10 (d, 1 H), 8.01–7.78 (m, 5 H), 7.65–7.54 (m, 2 H), 7.42–7.39 (d, 2 H), 7.25–7.19 (m, 1 H); $^{13}$C NMR (62.7 MHz) 190.2, 138.0, 135.8, 135.4, 135.2, 132.9, 132.7, 130.7, 130.0, 129.8, 129.0, 128.8, 128.0, 127.0, 124.6 ppm. Elemental Analysis. Calculated for $C_{19}H_{12}Cl_2O$: C, 69.74; H, 3.70. Found: C, 67.84; H, 3.78.

1,3-Di(2-naphthyl)propenone. (60) The reaction was stirred 5 hours, and a solid formed and was filtered. Recrystallization from 10% hexanes in chloroform afforded 1.66 g (53.9%) of a bright yellow powder: mp 201.3–202.6° C. (lit. mp 197–198° C., Levai, *Pharmazie*, 1979 34(7), 439). $^1$H NMR (250 MHz) δ 8.61 (s, 1 H), 8.18–7.80 (m, 11 H), 7.67–7.55 (m, 4 H).

1-(2-Naphthyl)-3-phenylpropenone. (61) After stirring 2 hours, a solid formed and was filtered. Recrystallization from ethanol afforded 1.98 g (76.7%) of yellow flakes: mp 104.2–104.8° C. (lit. mp 102° C., Braude and Gore, *J. Chem. Soc.*, 1959, 41–49). $^1$H NMR (250 MHz) δ 8.56 (s, 1 H), 8.15–8.11 (d, 1 H), 8.03–7.88 (m, 4 H), 7.74–7.68 (m, 4 H), 7.65–7.55 (m, 2 H), 7.46–7.43 (m, 2 H); $^{13}$C NMR (62.7 MHz) 190.5, 145.0, 135.7, 135.1, 132.7, 130.7, 130.1, 129.7, 129.2, 128.7, 128.6, 128.0, 127.0, 124.7, 122.2 ppm.

3-(2-Naphthyl)-1-phenylpropenone. (62) After stirring 3 hours, a solid formed and was filtered. Recrystallization from ethanol afforded 2.10 g (81.4%) of a yellow, flaky powder: mp 154–155° C. (lit. mp 155–156° C., Levai, supra). $^1$H NMR (250 MHz) δ 8.10–7.79 (m, 8 H), 7.69–7.50 (m, 6 H); $^{13}$C NMR (62.7 MHz) 190.7, 145.1, 138.5, 134.6, 133.5, 133.0, 132.5, 130.9, 128.8, 128.7, 128.0, 127.6, 127.0, 123.8, 122.4 ppm.

1-(2-Naphthyl)-3-(1-naphthyl)propenone. (63) The reaction stirred 3 hours. Recrystallization from ethanol afforded 2.62 g (85.1%) of yellow flakes: mp 159–160° C. (lit. mp 157–158° C., Levai, supra). $^1$H NMR (250 MHz) δ 8.79–8.73 (d, 1 H), 8.61 (s, 1 H), 8.32–8.29 (d, 1 H), 8.20–8.16 (d, 1 H), 8.04–7.91 (m, 5 H), 7.84–7.78 (d, 1 H), 7.67–7.53 (m, 6 H); $^{13}$C NMR (62.7 MHz) 190.2, 141.9, 135.7, 133.9, 132.8, 132.0, 131.0, 130.3, 128.7, 128.4, 127.2, 127.0, 126.5, 125.6, 125.3, 124.9, 124.7, 123.7 ppm.

1-(1-Naphthyl)-3-(2-naphthyl)propenone. (64) After stirring 3 hours, a viscous oil formed which sat at room temperature for 2 days. A solid formed which was recrystallized from ethyl acetate twice to afford 1.39 g (45.1%) of yellow flakes: mp 83.5–84.3° C. (lit. mp 84–85° C., Levai, supra). $^1$H NMR (250 MHz) δ 8.41–8.37 (m, 1 H), 8.05–7.74 (m, 9 H), 7.63–7.51 (m, 5 H), 7.47–7.40 (d, 1 H); $^{13}$C NMR (62.7 MHz) 195.7, 146.2, 137.3, 134.8, 134.1, 133.5, 132.3, 131.8, 131.0, 130.7, 129.0, 128.8, 128.7, 128.0, 127.7, 127.4, 127.3, 127.0, 126.7, 125.6, 124.7, 123.8 ppm.

3-Benzylidene-4-chromanone. (66) To a solution of benzaldehyde (430 mg, 4.05 mmol) and 4-chromanone (500 mg, 3.37 mmol) in 8.4 ml of ethanol heated almost to boiling was added 1.7 ml of concentrated hydrochloric acid dropwise. After refluxing for 2 days, the solution was cooled overnight, and a precipitate formed. The precipitate was recrystallized from ethanol to afford 367 mg (46.1%) of white flakes: mp 111.8–113.4° C. (lit. mp 112° C., Powell, *J. Am. Chem. Soc.*, 1923, 45, 2708–2711). $^1$H NMR (250 MHz) δ 8.06–8.02 (dd, 1 H), 7.90 (s, 1 H), 7.54–7.31 (m, 6 H), 7.09 (t, 1 H), 7.00–6.96 (d, 1 H), 5.37 (s, 2 H); $^{13}$C NMR (62.7 MHz) 182.4, 161.3, 137.7, 136.1, 134.6, 131.1, 130.2, 129.7, 128.9, 128.1, 122.1, 118.1, 67.8 ppm.

1-(1-Naphthyl)-3-phenylpropenone. (58) After stirring 3 hours, a viscous oil formed which was chromatographed with silica gel using a 9:1 hexanes:ether solvent. 850 mg (32.9%) of yellow flakes resulted: mp 105.5–106.7° C. (lit. mp 105° C., Bonsign, et al., *Gazz. Chim. Ital.*, 1976, 106, 617). $^1$H NMR (250 MHz) δ 8.37–8.33 (m, 1 H), 8.03–8.00 (d, 1 H), 7.95–7.90 (m, 1 H), 7.81–7.78 (d, 1 H), 7.68–7.49 (m, 6 H), 7.45–7.41 (m, 2 H), 7.36–7.29 (d, 1 H); $^{13}$C NMR (62.7 MHz) 195.9, 146.1, 137.3, 134.8, 134.0, 132.5, 131.8, 130.9, 129.2, 128.9, 127.5, 126.7, 125.6, 124.7 ppm.

1,3-Di(1-naphthyl)propenone. (65) After stirring 2 hours, a viscous oil formed which was chromatographed with silica gel using a 9:1 hexanes:ether solvent. A solid formed which was recrystallized from ethyl acetate to afforded 629 mg (20.4%) of yellow flakes: mp 74.5–75.0° C. (lit. mp 70.0–72.0° C. Matsui, et al., *J. Chem. Soc., Perkins Trans.* 2, 1992, 201–206). $^1$H NMR (250 MHz) δ 8.56–8.50 (d, 1 H), 8.49–8.44 (m, 1 H), 8.13–7.88 (m, 7 H), 7.65–7.50 (m, 6 H); $^{13}$C NMR (62.7 MHz) 195.5, 142.8, 137.3, 134.1, 133.9, 132.1, 131.2, 130.8, 129.6, 129.0, 128.7, 127.6, 127.2, 126.7, 126.4, 125.9, 125.7, 125.4, 124.7, 123.4 ppm.

2-Benzylidenetetralone. (68) The solution turned purple when the base was added, and in 5 hours a sea-green-colored precipitate formed. Recrystallization from ethanol afforded 1.56 g (66.7%) of small, yellow, flaky crystals: mp 106.2–106.6° C. (lit. mp 108° C., Riahi, et al., supra). $^1$H NMR (250 MHz) δ 8.17–8.14 (m, 1 H), 7.89 (s, 1 H), 7.53–7.24 (m, 8 H), 3.14 (t, 2 H), 2.95 (t, 2 H); $^{13}$C NMR (62.7 MHz) 188.1, 143.4, 136.0, 135.6, 133.5, 130.1, 128.7, 128.4, 127.2, 29.1, 27.4 ppm.

2-(2,6-Dichlorobenzylidene)tetralone. (69) 30 ml of ethanol was used to dissolve the starting materials. The solution turned purple when the base was added, and in 4 hours a purple oil formed. Chromatography with silica gel using 9:1 hexanes:ethyl acetate afforded a yellow oil. Upon standing at 4° C., a solid formed and was recrystallized from ethanol yielding 2.00 g (66.0%) of faint-yellow platelets: mp 73.8–75.6° C. $^1$H NMR (250 MHz) δ 8.20–8.17 (d, 1 H), 7.60 (s, 1 H), 7.50 (t, 1 H), 7.40–7.37 (m, 3 H), 7.26–7.19 (m, 2 H), 2.97 (t, 2 H), 2.68 (t, 2 H); $^{13}$C NMR (62.7 MHz) 187.0, 144.1, 139.7, 134.8, 134.2, 133.7, 133.4, 130.8, 129.6, 128.5, 128.2, 127.2, 28.8, 28.0 ppm. Elemental Analysis. Calculated for $C_{17}H_{12}Cl_2O$: C, 67.34; H, 4.00. Found: C, 67.94; H, 4.27.

2-(1-Naphthylidene)tetralone. (70) A 5 mmol scale reaction was performed. The solution became dark purple when the base was added. After stirring the reaction about 14 hours, the solution turned red with a yellow precipitate, which was a rock-hard solid. The solid was pulverized with a mortal and pestle and was recrystallized from ethanol affording 1.10 g (77.7%) of small, light-yellow needles: mp 129.7–131.6° C. $^1$H NMR (250 MHz) δ 8.40 (s, 1 H), 8.25–8.22 (m, 1 H), 8.03 (t, 1 H), 7.94–7.87 (m, 2 H), 7.58–7.38 (m, 6 H), 7.27–7.25 (d, 1 H), 3.04–2.91 (m, 4 H); $^{13}$C NMR (62.7 MHz) 188.0, 143.8, 137.6, 134.6, 133.5, 133.3, 132.2, 129.1, 128.7, 128.5, 127.3, 126.8, 126.7, 126.4, 125.3, 125.0, 29.4, 27.9 ppm. Elemental Analysis. Calculated for $C_{21}H_{16}O$: C, 88.69; H, 5.68. Found: C, 88.54; H, 5.64.

2-(2-Naphthylidene)tetralone. (71) The reaction was stirred 3 hours. Recrystallization from ethanol afforded 1.23 g (43.3%) of bright-yellow needles: mp 136.4–136.8° C. (lit. mp 134° C., Riahi, et al, supra). $^1$H NMR (250 MHz) δ 8.21–8.18 (d, 1 H), 8.05 (s, 1 H), 7.92–7.85 (m, 4 H), 7.58–7.48 (m, 4 H), 7.39 (t, 1 H), 7.28–7.25 (d, 1 H), 3.23 (t, 2 H), 2.96 (t, 2 H); $^{13}$C NMR (62.7 MHz) 188.0, 143.3, 136.9, 135.6, 133.5, 133.2, 129.8, 128.5, 128.4, 128.2, 127.9, 127.4, 127.2, 127.0, 126.6, 29.0, 27.5 ppm.

2,6-Di(benzylidene)cyclohexanone. (75) Cyclohexanone (10 mmol) and benzaldehyde (20 mmol) were used. The reaction stirred for 2 hours. A solid formed and was filtered. Recrystallization from ethanol yielded 2.01 g (73.4%) of bright-yellow flakes: mp 118.1–119.0° C. (lit. mp 116–117° C., Smith, et al., *Can. J. Chem.*, 1973, 51, 1458–1470). $^1$H NMR (250 MHz) δ 7.83 (s, 2 H), 7.50–7.32 (m, 10 H), 2.95 (t, 4 H), 1.80 (p, 2 H); $^{13}$C NMR (62.7 MHz) 190.5, 137.1, 136.4, 136.1, 130.5, 128.8, 128.5, 28.6, 23.2 ppm.

2,6-Bis(2,6-dichlorobenzylidene)cyclohexanone. (76) Cyclohexanone (10 mmol), 60 ml of ethanol, and 2,6-dichlorobenzaldehyde (20 mmol) were used. The reaction stirred for 4 hours. A solid formed and was filtered. Recrystallization from ethanol yielded 3.24 g (78.6%) of bright-yellow flakes: mp 185.0–186.0° C. (lit. mp 183° C., Smith et al., supra). $^1$H NMR (250 MHz) δ 7.60 (s, 2 H), 7.37–7.18 (m, 6 H), 2.45 (t, 4 H), 1.73 (p, 2 H); $^{13}$C NMR (62.7 MHz) 188.2, 140.3, 134.6, 134.4, 132.4, 129.6, 128.1, 28.4, 22.1 ppm.

Other enone derivatives. Other derivatives synthesized have specific reaction conditions as set forth hereinbelow.

1,5-Diphenyl-1E,4E-pentadien-3-one. (3) Hill and Barbaro, *Experiments in Organic Chemistry*. Contemporary Publishing Co. of Raleigh, Inc., Raleigh, 1996. 5 g of sodium hydroxide, dissolved in 25 ml of water and 25 ml of 95% ethanol, was cooled to 20 to 25° C. 2.9 g (50 mmol) of acetone and 10.6 g (100 mmol) of benzaldehyde were added, and a yellow precipitate formed. After 20 minutes the solution was filtered, and the solid was recrystallized from ethyl acetate to afford 10.1 g (86.3%) of bright-yellow platelets: mp 111.9–112.5° C. (lit. mp 112° C., Hill and Barbaro, supra). $^1$H NMR (250 MHz) δ 7.79–7.73 (d, 1 H), 7.65–7.61 (m, 4 H), 7.44–7.41 (t, 6 H), 7.13–7.07 (d, 1 H) ppm.

2-Benzylidene-1,3-indandione. (8) (*Chem. Pharm. Bull.* 1974, 22(2), 448–451). Boron oxide (720 mg, 10.26 mmol) and benzaldehyde (800 mg, 7.53 mmol) were added to a stirred solution of the indandione (1.00 g, 6.84 mmol) and piperidine (3 drops) in 10.2 ml of benzene. The solution was refluxed with stirring for 30 minutes. After filtration of the solution, the filtrate was concentrated under reduced pressure. The resulting crystalline solid was recrystallized from ethanol to afford 1.00 g (62.4%) of yellowish-green platelets: mp 149.5–150.0° C. (lit. mp 150° C., Okukawa, et al., *Chem. Pharm. Bull.*, 1974, 22(2), 448–451). $^1$H NMR (250 MHz) δ 8.47–8.45 (m, 2 H), 8.06–7.99 (m, 2 H), 7.90 (s, 1 H), 7.84–7.79 (m, 2 H), 7.58–7.50 (m, 3 H); $^{13}$C NMR (62.7 MHz) 190.5, 189.2, 147.2, 142.7, 140.2, 135.6, 135.4, 134.3, 133.4, 133.2, 129.3, 129.0, 123.5, 123.5 ppm.

2,6-Dichlorochalcone. (31) (*Canadian Journal of Chemistry*. 1968 46, 1952–6). To a solution of 2,6-dichlorobenzaldehyde (1.75 g, 10.0 mmol) and acetophenone (1.20 g, 10.0 mmol) in 30.0 ml of methanol was added 4.4 ml of 40% sodium hydroxide in water at 10° C. After stirring for 3 hours at room temperature, a solid appeared and was filtered. The precipitate was recrystallized from methanol to afford 1.68 g (60.6%) of yellow needles: mp 84.5–85.3° C. (lit. mp 83° C. Kuck and Grutzmacher, *Org. Mass. Spect.* 1978, 13, 90–102). $^1$H NMR (250 MHz) δ 8.05–8.01 (m, 2 H), 7.90–7.84 (d, 1 H), 7.70–7.64 (d, 1 H), 7.62–7.48 (m, 3 H), 7.41–7.37 (d, 2 H), 7.24–7.18 (dd, 1 H); $^{13}$C NMR (62.7 MHz) 190.3, 139.0, 135.3, 133.3 132.8, 130.7, 130.0, 129.0, 128.9 ppm.

2,2',6,6'-Tetrachlorochalcone. (32) To a solution of the 2,6-dichlorobenzaldehyde (438 mg, 2.50 mmol) and 2,6-dichloroacetophenone (473 mg, 2.50 mmol) in 3.7 ml of ethanol was added 0.1 ml of 40% sodium hydroxide in water at 10° C. After stirring for 2 hours at room temperature, a solid appeared and was filtered. The precipitate was recrystallized from methanol to afford 465 mg (53.8%) of white, cottony needles: mp 130–130.4° C. (lit. mp 124–125° C., Kaiser, et al., *Monatshefte fur Chemie*, 1997, 128, 1247–1254). $^1$H NMR (250 MHz) δ 7.43–7.17 (m, 7 H), 7.10–7.03 (d, 1 H); $^{13}$C NMR (62.7 MHz) 193.0, 141.7, 137.5, 135.3 134.4, 132.1, 131.8, 131.0, 130.6, 129.0, 128.3 ppm.

2',6'-Dichlorochalcone. (33) To a solution of benzaldehyde (141 mg, 1.32 mmol) and 2,6-dichloroacetophenone (250 mg, 1.32 mmol) in 2.0 ml of methanol was added 0.1 ml of 40% sodium hydroxide in water at 10° C. After stirring for 3 hours at room temperature, a solid appeared and was filtered. The precipitate was recrystallized from ethanol to afford 174 mg (47.5%) of small, white needles: mp 108.0–109.0° C. (lit. mp 105–107, Batt, et al., *J. Med. Chem.*, 1993, 36, 1434–1442). $^1$H NMR (250 MHz) δ 7.57–7.54 (m, 2 H), 7.45–7.24 (m, 7 H), 7.00–6.94 (d, 1 H).

2,2',3,3',4,4',5,5',6,6'-Decafluorochalone. (34) Matoba and Yamazaki, *Chem. Pharm. Bull.*, 1982, 30(7), 2586–2589. 100 mg of sodium hydroxide was added to 4.2 ml of water and 3.2 ml of 95% ethanol. To 1.9 ml of the above solution in an ice bath was added 2,3,4,5,6-pentafluoroacetophenone (500 mg, 2.38 mmol) and then 2,3,4,5,6-pentafluorobenzaldehyde (467 mg, 2.38 mmol). After stirring for 2 hr at room temperature, a yellow solid appeared and was filtered. The precipitate was recrystallized from ethanol twice to afford 550 mg (59.5%) of a white powder: mp 58.0–59.0° C. (lit. mp 58.4–59.0° C., Filler, et al., *J. Org. Chem*, 1975, 40, 935–939). $^1$H NMR (250 MHz) δ 7.66–7.59 (d, 1 H), 7.37–7.30 (d, 1 H); $^{13}$C NMR (62.7 MHz) 183.1, 148.3, 146.9, 144.2, 142.6, 140.1, 136.1, 132.1, 130.3, 114.2, 109.7.

2,3,4,5,6-Pentafluorochalone. (35) 660 mg of sodium hydroxide was added to 6.0 ml of water and 3.0 ml of 95% ethanol. To 1.7 ml of the above solution in an ice bath was added acetophenone (306 mg, 2.56 mmol) and then 2,3,4,5,6-pentafluorobenzaldehyde (500 mg, 2.56 mmol). After stirring for 2 hr at room temperature, a yellow solid appeared and was filtered. The precipitate was recrystallized from ethanol to afford 148 mg (19.4%) of a white powder: mp 145.1–146.6° C. (lit. mp 144–146° C., Filler, et al., supra). $^1$H NMR (250 MHz) δ 8.05–8.01 (m, 2 H), 7.91–7.84 (d, 1 H), 7.80–7.73 (d, 1 H), 7.67–7.51 (m, 3 H); $^{13}$C NMR (62.7 MHz) 189.6, 144.0, 140.0, 133.7, 129.1, 128.9, 128.0.

2',3',4',5',6'-Pentafluorochalone. (36) 100 mg of sodium hydroxide was added to 4.2 ml of water and 3.2 ml of 95% ethanol. To 1.9 ml of the above solution in an ice bath was added 2,3,4,5,6-pentafluoroacetophenone (500 mg, 2.38 mmol) and then benzaldehyde (252 mg, 2.38 mmol). After stirring for 1 hr at room temperature, a yellow solid appeared and was filtered. The precipitate was washed with cold 95% ethanol twice to afford 543 mg (76.5%) of a white powder: mp 98.2–99.2° C. (lit. mp 102.2–102.9° C., Filler et al., supra). $^1$H NMR (250 MHz) δ 7.61–7.40 (m, 6 H), 7.08–7.01 (d, 1 H); $^{13}$C NMR (62.7 MHz) 184.1, 148.5, 133.8, 131.9, 129.4, 129.1, 126.3.

2,2',6,6'-Tetramethoxychalcone. (37) To a solution of 2,6-dimethoxybenzaldehyde (250 mg, 1.50 mmol) and 2,6-tetramethoxyacetophenone (271 mg, 1.50 mmol) in 2.2 ml of methanol was added 1.0 ml of 40% sodium hydroxide in water at 10° C. After stirring for 5 hours at room temperature, a solid formed. Recrystallization form methanol provided 483 mg (98.0%) of a white powder: mp 179.0–179.8° C. $^1$H NMR (250 MHz) δ 7.85–7.77 (d, 1 H), 7.45–7.38 (d, 1 H), 7.33–7.21 (m, 2 H), 6.62–6.59 (d, 2 H), 6.54–6.50 (d, 2 H), 3.82 (s, 6 H), 3.77 (s, 6 H); $^{13}$C NMR (62.7 MHz) 197.4, 160.3, 157.7, 137.1, 131.7, 131.5, 130.4, 119.2, 112.8, 104.2, 103.8, 56.1, 55.9 ppm. Elemental Analysis. Calculated for $C_{19}H_2O_5$: C., 69.49; H, 6.15. Found: C, 69.44; H, 6.10.

2',6'-Dimethoxychalcone. (38) To a solution of benzaldehyde (295 mg, 2.77 mmol) and 2,6-dimethoxyacetophenone (500 mg, 2.77 mmol) in 4.1 ml of methanol was added 0.1 ml of 40% sodium hydroxide in water at 10° C. After stirring for 3 hour at room temperature, a solid appeared and was filtered. The precipitate was recrystallized from methanol to afford 371 mg (49.9%) of white flakes: mp 125.5–126.6° C.

(lit. mp 123–124° C., Kuck and Grutzmacher, *Org. Mass. Spect.,* 1978, 13, 90–102). $^1$H NMR (250 MHz) δ 7.55–7.51 (m, 2 H), 7.39–7.30 (m, 5 H), 7.00–6.94 (d, 1 H), 6.64–6.61 (d, 2 H), 3.79 (s, 6 H); $^{13}$C NMR (62.7 MHz) 213. 176.1, 163.9, 153.4, 149.4, 149.0, 147.4, 147.3, 147.0, 122.6, 74.5 ppm.

2,6-Dimethoxychalcone. (39) To a solution of 2,6-dimethoxybenzaldehyde (250 mg, 1.50 mmol) and acetophenone (180 mg, 1.50 mmol) in 2.2 ml of methanol was added 1.0 ml of 40% sodium hydroxide in water at 10° C. After stirring overnight at room temperature, a solid precipitated. The precipitate was recrystallized from methanol to afford 350 mg (87.1%) of a white, flaky solid: mp 54.9–55.8° C. (lit. mp 54–55° C., Noyce and Jorgenson, *J. Am. Chem. Soc.,* 1963, 85, 2420–2426). $^1$H NMR (250 MHz) δ 8.33–8.26 (d, 1 H), 8.05–7.97 (m, 3 H), 7.57–7.49 (m, 3 H), 7.30 (m, 1 H), 6.61–6.57 (d, 2 H), 3.92 (s, 6 H); $^{13}$C NMR (62.7 MHz) 192.3, 160.6, 139.2, 136.0, 132.4, 131.7, 128.6, 125.1, 113.1, 105.8, 103.9, 56.0 ppm.

2,6-Dichloro-2',6'-dimethoxychalcone. (40) To a solution of 2,6-dichlorobenzaldehyde (485 mg, 2.77 mmol) and 2,6-dimethoxyacetophenone (500 mg, 2.77 mmol) in 4.1 ml of methanol was added 1.0 ml of 40% sodium hydroxide in water at 10° C. After stirring for 1.5 hours at room temperature, a solid appeared and was filtered. The precipitate was recrystallized from methanol to afford 481 mg (51.5%) of faint-yellow needles: mp 126.8–127.8° C. $^1$H NMR (250 MHz) δ 7.48–7.42 (d, 1 H), 7.37–7.31 (m, 3 H), 7.11–7.04 (d, 1 H), 6.63–6.60 (d, 2 H), 3.81 (s, 6 H); $^{13}$C NMR (62.7 MHz) 195.1, 158.0, 138.4, 136.5, 135.2, 132.6, 131.4, 130.0, 129.0, 117.9, 104.2, 56.1 ppm. Elemental Analysis. Calculated for $C_{17}H_{14}Cl_2O_3$: C, 60.55; H, 4.19. Found: C, 60.60; H, 4.18.

1,3-Di(2-pyridyl)propenone. (46) To an ice-cold solution of pyridine-2-carboxaldehyde (442 mg, 4.13 mmol) and 2-acetylpyridine (500 mg, 4.13 mmol) in 10.3 ml of ethanol was added dropwise 2.1 ml of concentrated hydrochloric acid. The reaction stirred for 1.5 hours in an ice bath. After stirring for 6 hours at room temperature, the solution was placed in an ice bath and was neutralized with 40% sodium hydroxide. A standard ether work up yielded the crude product, which was chromatographed on a column with silica gel using 2:1 hexanes:ethyl acetate to afford 253 mg (29.1%) of a light-yellow solid that turned light green on standing (purity was not affected): mp 66.2–67.2° C. (lit. mp 62–64° C., Marvel, et al, *J. Org. Chem.,* 1955, 20, 1785–1792). $^1$H NMR (250 MHz) δ 8.68–8.60 (m, 3 H), 8.12–8.09 (d, 1 H), 7.88–7.40 (m, 5 H), 7.23–7.19 (m, 1 H); $^{13}$C NMR (Liptaj, et al., *J. Collection Czechoslovak Chem. Comun.* 1981, 46, 1486–1491) (62.7 MHz) 189.9, 154.0, 153.9, 148.1, 143.1, 137.1, 136.9, 127.2, 125.1, 124.8, 124.4, 122.2 ppm.

1-Phenyl-3-(2-pyridyl)propenone. (47) To a stirred solution of pyridine-2-carboxaldehyde (500 mg, 4.67 mmol) in 7.0 ml of dry methylene chloride was added benzoylmethylene triphenylphosphorane (1.95 g, 5.14 mmol). The mixture was stirred overnight. The solution was concentrated by evaporation to afford the crude product. Chromatography on a column with silica gel using 4:1 ethyl acetate:hexanes provided 850 mg (91.9%) of a light-yellow powder: mp 60.5–61.7° C. (lit. mp 60–61° C., Marvel, et al, supra). $^1$H NMR (250 MHz) δ 8.69–8.67 (d, 1 H), 8.16–8.08 (m, 3 H), 7.80–7.70 (m, 2 H), 7.62–7.46 (mn, 4 H), 7.32–7.25 (m, 1 H); $^{13}$C NMR (62.7 MHz) 190.6, 153.2, 150.2, 142.7, 137.9, 137.2, 133.3, 128.9, 125.8, 125.6, 124.6 ppm.

1-Phenyl-3-(3-pyridyl)propenone. (48) To a stirred solution of pyridine-3-carboxaldehyde (500 mg, 4.67 mmol) in 7.0 ml of dry methylene chloride was added benzoylmethylene triphenylphosphorane (1.95 g, 5.14 mmol). The mixture was stirred overnight. The solution was concentrated by evaporation to afford the crude product. Recrystallization from diethyl ether provided 295 mg (31.9%) of a light-yellow powder: mp 102.7–103.7° C. (lit. mp 101–102, Marvel, et al., supra). $^1$H NMR (250 MHz) δ 8.86 (s, 1 H), 8.64–8.63 (d, 1 H), 8.06–7.93 (m, 3 H), 7.83–7.76 (d, 1 H), 7.63–7.49 (m, 4 H), 7.39–7.34 (m, 1 H); $^{13}$C NMR (62.7 MHz) 190.0, 151.3, 150.1, 141.1, 137.9, 134.8, 133.3, 130.6, 126.9, 126.7, 124.0 ppm.

3-Phenyl-1-(2-pyrrolyl)propenone. (49) To a solution of benzaldehyde (486 mg, 4.58 mmol) and 2-acetylpyrrole (500 mg, 4.58 mmol) in 2 ml of ethanol was added dropwise 0.5 ml of 10% sodium hydroxide at room temperature. After stirring 2 hours, the solution was filtered. The precipitate was recrystallized from 90% ethanol to afford 743 mg (82.6%) of the product: mp 140.1–141.1° C. (lit. mp 140–142, Matoba and Yamazaki, supra). $^1$H NMR (250 MHz) δ 10.30 (b s, 1 H), 7.90–7.84 (d, 1 H), 7.68–7.64 (m, 2 H), 7.48–7.37 (m, 4 H), 7.18–7.11 (m, 1 H), 6.39–6.36 (m, 1 H); $^{13}$C NMR (62.7 MHz) 179.1, 142.4, 135.2, 133.3, 130.4, 129.1, 128.5, 125.9, 122.2, 116.8, 111.1 ppm.

1-Phenyl-3-(2-pyrrolyl)propenone. (50) To a solution of the acetophenone (630 mg, 5.26 mmol) and pyrrole-2-carboxaldehyde (500 mg, 5.26 mmol) in 2.1 ml of ethanol was added 0.5 ml of 10% sodium hydroxide at room temperature. After stirring overnight, the solution was filtered. The precipitate was recrystallized from 90% ethanol to afford 500 mg (48.5%) of the product: mp 136.6–137.4° C. (lit. mp 138–139° C., Lubrzynska, *J. Chem. Soc.,* 1916, 1118). $^1$H NMR (250 MHz) δ 9.19 (b s, 1 H), 8.01–7.97 (m, 2 H), 7.81–7.75 (d, 1 H), 7.60–7.45 (m, 3 H), 7.22–7.16 (d, 1 H), 7.01 (s, 1 H), 6.73 (s, 1 H), 6.36–6.33 (m, 1 H); $^{13}$C NMR (62.7 MHz) 190.9, 135.1, 132.6, 128.8, 128.5, 123.5, 116.0, 115.6, 111.7 ppm.

1-(9-Anthryl)-3-phenylpropenone. (51) To a solution of benzaldehyde (241 mg, 2.27 mmol) and 9-acetylanthracene (500 mg, 2.27 mmol) in 10 ml ethanol was added 2.3 ml of 40% potassium hydroxide in water at 10° C. After stirring for 3 hours at room temperature, the solution was filtered. The precipitate was recrystallized from ethanol to afford 604 mg (86.3%) of a bright-yellow powder: mp 203.3–204.6° C. (lit. mp 201–204° C., Batt, et al., supra). $^1$H NMR (250 MHz) δ 8.56 (s, 1 H), 8.09–8.05 (m, 2 H), 7.95–7.91 (m, 2 H), 7.53–7.20 (m, 11 H); ); $^{13}$C NMR (62.7 MHz) 200.5, 148.2, 134.4, 131.2, 129.3, 129.1, 128.9, 128.8, 126.8, 125.7, 125.4 ppm.

3-(9-Anthryl)-1-phenylpropenone. (52) To a solution of 9-anthraldehyde (500 mg, 2.42 mmol) and acetophenone (291 mg, 2.42 mmol) in 10.0 ml ethanol was added 2.3 ml of 40% potassium hydroxide in water at room temperature. After stirring for 3 hours, a solid formed and was recrystallized from ethanol to afford 508 mg (68.1%) of long, yellowish-orange needles: mp 124.6–125.4° C. (lit. mp 124–125° C., Wiley, *J. Org. Chem.,* 1958, 23, 732–735). $^1$H NMR (250 MHz) δ 8.85–8.79 (d, 1 H), 8.48 (s, 1 H), 8.34–8.31 (m, 2 H), 8.13–8.01 (m, 4 H), 7.66–7.48 (m, 8 H); $^{13}$C NMR (62.7 MHz) 189.9, 142.1, 138.1, 133.3, 131.5, 131.2, 130.3, 129.8, 129.1, 128.9, 128.6, 126.6, 125.6, 125.5 ppm.

1,3-Di(9-Anthryl)propenone. (53) To a solution of 9-anthraldehyde (468 mg, 2.27 mmol) and 9-acetylanthracene (500 mg, 2.27 mmol) in 9.9 ml ethanol was added 2.3 ml of 40% potassium hydroxide in water at room temperature. After stirring for 3 hours, a solid formed and was recrystallized twice from methylene chloride to afford 500 mg (53.9%) of a bright-yellow powder: mp 298.9–299.5° C. (lit. mp 299–300° C., Itoh, et al., *J. Phys. Chem.*, 1992, 96, 5759–5765). $^1$H NMR (250 MHz) δ 8.62 (s, 1 H), 8.42 (s, 1 H), 8.23–8.11 (m, 5 H), 8.01–7.93 (m, 4 H), 7.65–7.54 (m, 4 H), 7.46–7.39 (m, 4 H), 7.31–7.25 (d, 1 H) ppm.

1-(9-Anthryl)-3-(2-naphthyl)propenone. (54) To a solution of naphthaldehyde (355 mg, 2.27 mmol) and 9-acetylanthracene (500 mg, 2.27 mmol) in 10 ml ethanol was added 1.0 ml of 40% potassium hydroxide in water at 10° C. After stirring for 10 minutes at room temperature, a polymer-like material formed and was recrystallized from ethanol to afford 490 mg (60.2%) of a bright-yellow powder: mp 158.5–159.4° C. $^1$H NMR (250 MHz) δ 8.58 (s, 1 H), 8.12–8.07 (m, 2 H), 8.01–7.97 (m, 2 H), 7.83–7.66 (m, 5 H), 7.55–7.42 (m, 8 H); $^{13}$C NMR (62.7 MHz) 200.5, 148.3, 134.8, 134.7, 133.3, 131.9, 129.5, 128.9, 128.8, 127.9, 127.8, 127.0, 126.8, 126.7, 125.7, 125.5, 123.6 ppm. Elemental Analysis. Calculated for $C_{27}H_{18}O$: C, 90.46; H, 5.07. Found: C, 90.39; H, 5.06.

1,3-Bis(4-biphenyl)propenone. (55) To a 40° C. solution of 4-biphenylcarboxaldehyde (465 mg, 2.55 mmol) and 4-acetylbiphenyl (500 mg, 2.55 mmol) in 20 ml ethanol was added 2.5 ml of 40% potassium hydroxide in water. After stirring for 3 hours at room temperature, the solution was filtered. The precipitate was recrystallized from ethyl acetate to afford 592 mg (64.4%) of small, yellow needles: mp 197–198° C. (lit.[101] mp 195–197° C.). $^1$H NMR (250 MHz) δ 8.17–8.13 (d, 2 H), 7.95–7.89 (d, 1 H), 7.78–7.61 (m, 11 H), 7.64–7.37 (m, 6 H); $^{13}$C NMR (62.7 MHz) 190.1, 145.8, 144.6, 143.6, 140.4, 140.2, 134.1, 129.4, 129.2, 128.5, 128.2, 127.9, 127.5, 127.3, 122.0 ppm.

1-(4-Biphenyl)-3-phenylpropenone. (56) To a 40° C. solution of benzaldehyde (270 mg, 2.55 mmol) and 4-acetylbiphenyl (500 mg, 2.55 mmol) in 20 ml ethanol was added 2.5 ml of 40% potassium hydroxide in water. After stirring for 15 minutes, the solution was filtered. The precipitate was recrystallized from ethanol to afford 347 mg (47.9%) of off-white flakes: mp 153–154° C. (lit. mp 156–158° C., Cromwell, et al., *J. Am. Chem. Soc.*, 1957, 73, 922–926). $^1$H NMR (250 MHz) δ 8.15–8.12 (d, 2 H), 7.91–7.85 (d, 1 H), 7.77–7.40 (m, 13 H); $^{13}$CNMR (62.7 MHz) 190.1, 145.7, 144.9, 140.1, 137.1, 135.1, 130.7, 129.3, 129.2, 128.9, 128.4, 127.5, 122.2 ppm.

3-(4-Biphenyl)-1-phenylpropenone. (57) To a 40° C. solution of 4-biphenylcarboxaldehyde (500 mg, 2.74 mmol) and acetophenone (330 mg, 2.74 mmol) in 4.1 ml ethanol was added 2.7 ml of 40% potassium hydroxide in water. After stirring for 4 hours, the solution was filtered. The precipitate was recrystallized from ethanol to afford 405 mg (52.0%) of yellow flakes: mp 112.0–112.6° C. (lit. mp 111–112° C., Wiley, et al., supra). $^1$H NMR (250 MHz) δ 8.09–8.06 (d, 2 H), 7.92–7.86 (d, 1 H), 7.76–7.37 (m, 13 H); $^{13}$C NMR (62.7 MHz) 190.6, 144.5, 143.4, 140.2, 136.4, 134.0, 132.9, 129.1, 128.8, 128.7, 128.1, 127.7, 127.1, 122.0 ppm.

1,5-Di(2-chloro-6-fluorophenyl)-1E,4E-pentadien-3-one. (72) To a solution of the 2-chloro-6-fluoro-benzaldehyde (1.59 g, 10.0 mmol) and acetone (290 mg, 5.00 mmol) in 15 ml of ethanol was added 5 ml of 40% potassium hydroxide at 10° C. After stirring for several hours at room temperature, the solution was filtered. The precipitate was recrystallized from ethanol to afford 879 mg (51.7%) of a light-yellow powder: mp 143.5–144.3° C. $^1$H NMR (250 MHz) δ 7.98–7.91 (d, 2 H), 7.36–7.22 (m, 6 H), 7.13–7.03 (m, 2 H); $^{13}$C NMR (62.7 MHz) 189.6, 134.0, 132.1, 131.8, 131.2, 131.0, 126.3, 115.4, 115.0 ppm. Elemental Analysis. Calculated for $C_{17}H_{10}Cl_2F_2O_5$: C, 60.20; H, 2.98. Found: C, 60.07; H, 2.99

1,5-Bis(2,6-dichlorophenyl)-1E,4E-pentadien-3-one. (73) To a 0.33 M solution of 2,6-dichlorobenzaldehyde (1.75 g, 10 mmol) and acetone (290 mg, 5 mmol) in 30 ml of ethanol was added 5 ml of 40% potassium hydroxide at 10° C. After stirring for 18 hr at room temperature, a solid precipitated and was filtered. The precipitate was recrystallized from ethanol to afford 1.46 g (78.5%) of pale yellow, cotton-like flakes: mp 154.0–154.4° C. (lit. mp 145–146° C., Unterhalt, *Arch. Pharm.*, 1978, 311, 262–267). $^1$H NMR (250 MHz) δ 7.85–7.79 (d, 2 H), 7.40–7.36 (d, 4 H), 7.26–7.19 (d, 2 H), 7.24–7.18 (m, 2 H); $^{13}$C NMR (62.7 MHz) 189.1, 137.6, 135.4, 133.3, 132.5, 130.2, 129.1 ppm.

1,5-Di(2-furyl)-1E,4E-pentadien-3-one. (74) 5 g of sodium hydroxide, dissolved in 25 ml of water and 25 ml of 95% ethanol, was cooled to 20 to 25° C. 2.9 g (50 mmol) of acetone and 10.6 g (100 mmol) of furaldehyde were added, and an oil formed. After 30 minutes the solution was neutralized with 10% hydrochloric acid and extracted with chloroform. The chloroform extracts were washed with brine, dried with magnesium sulfate, and evaporated to afford 2.08 g (97.2%) of orangish-red oil. $^1$H NMR (250 MHz) δ 7.85–7.79 (d, 1 H), 7.40–7.36 (m, 4 H), 7.26–7.18 (m, 4 H); $^{13}$C NMR (62.7 MHz) 189.1, 137,6 135.4, 133.3, 132.5, 130.2, 129.1 ppm.

2,6-Di(1-naphthylidene)cyclohexanone. (77) To a solution of the 1-naphthaldehyde (1.56 g, 10.0 mmol) and cyclohexanone (491 mg, 5.0 mmol) in 2.5 ml of ethanol was added 1.0 ml 10% sodium hydroxide at 0° C. After stirring for 12 hr at room temperature, the solution was filtered. The precipitate was recrystallized from ethyl acetate to afford 1.35 g (72.2%) of bright-yellow flakes: mp 211.8–213.1° C. (lit. mp 212° C., Aizenshtat, et al., *J. Org. Chem.*, 1977, 42, 2386–2394). $^1$H NMR (250 MHz) δ 8.46 (s, 2 H), 8.09 (m, 2 H), 7.89 (t, 4 H), 7.61–7.46 (m 6 H), 2.82 (t, 4 H), 1.71 (p, 2 H); $^{13}$C NMR (62.7 MHz) 190.3, 138.5, 135.5, 133.7, 133.3, 132.2, 129.1, 128.7, 127.2, 126.6, 126.4, 125.2, 125.0, 29.0, 23.8 ppm.

2,6-Di(2-naphthylidene)cyclohexanone. (78) To a solution of the 2-naphthaldehyde (1.56 g, 10.0 mmol) and cyclohexanone (491 mg, 5.0 mmol) in 7.5 ml of ethanol was added 5 ml 40% sodium hydroxide at 0° C. After stirring for 12 hr at room temperature, the solution was filtered. The precipitate was recrystallized from ethyl acetate to afford 1.50 g (80.6%) of bright-yellow flakes: mp 179.4–180.6° C. (lit. mp 176° C., Kabli, et al., *Indian J. Chem., Sect. B*, 1986, 25, 152–156). $^1$H NMR (250 MHz) δ 8.00–7.84 (m, 10 H), 7.62–7.48 (m, 6 H), 3.07 (t, 4 H), 1.85 (p, 2 H); $^{13}$C NMR (62.7 MHz) 190.4, 137.3, 136.5, 133.7, 133.3, 130.5, 128.5, 128.1, 127.9, 127.1, 126.6, 28.6, 23.7 ppm.

2,6-Di(2-pyridylidene)cyclohexanone. (79) To a 1 M solution of the pyridine-2-carboxaldehyde (500 mg, 4.67 mmol) and cyclohexanone (229 mg, 2.33 mmol) in 2.3 ml ethanol was added 1.0 ml of an aqueous 10% sodium hydroxide solution. After stirring for 12 hours at room temperature, water was added and was extracted with ether. A standard ether work-up provided the crude product. Column chromatography with silica gel using 1:1 hexanes:ethyl acetate afforded 140 mg (21.7%) of a flaky, yellow solid: mp 125.6–126.8° C. (lit. mp 127° C., Harries and Lenart, *Justus Liebigs Ann. Chem.*, 1915, 410, 113). $^1$H NMR (250 MHz) δ 8.70–8.69 (d, 2 H), 7.74–7.68 (m, 4 H), 7.45–7.42 (d, 2 H), 7.22–7.17 (m, 2 H), 3.32–3.27 (t, 4 H), 1.86–1.78 (p, 2 H); $^{13}$C NMR (62.7 MHz) 191.6, 155.7, 149.7, 140.2, 136.3, 134.2, 127.3, 122.8, 28.6, 22.4 ppm. Elemental Analysis. Calculated for $C_{18}H_{16}N_2O$: C, 78.22; H, 5.85; N, 10.14. Found: C, 78.18; H, 5.82; N, 10.14.

Benzalacetone (Fumiss, et a., *Vogel's Textbook of Practical Organic Chemistry, Fifth Ed.* New York; John Wiley & Sons, Inc., 1989. p. 1033)—To a stirred solution of 42.5 g (0.400 mol) of benzaldehyde and 63.5 g (1.1 mol) of acetone in a 250-ml round-bottom flask in an ce bath was added dropwise 10 ml of a 10% NaOH solution over 30 minutes. The mixture was not allowed to exceed 30° C. during the addition and was stirred for an additional 2 hours at room temperature after the addition. The reaction was quenched with dilute HCl until it rendered litmus paper slightly acidic. The aqueous layer was extracted with 20 ml of toluene, and the combined organic extracts were washed with water, dried with $MgSO_4$, and filtered. The toluene was removed by fractional distillation at atmospheric pressure, and benzalacetone was collected at 150–160° C. at 25 mmHg as a yellow liquid that solidified on standing at room temperature. The p.m.r. spectrum ($CDCl_3$, TMS) shows peaks at ppm 2.32 (s, 3H, Me), 6.67 (d, 1H, =CHCO), 7.44 (d, 1H, Ph—CH=) and 7.21–7.62 (m, 5H, Ar—H).

PREPARATION OF DIBENZALACETONE (Hill, R. K.; Barbaro, J. *Experiments in Organic Chemistry* Raleigh, N.C.; Contemporary Publishing Co. of Raleigh, Inc., 1996. E12-1–E12-3)—5 g of NaOH, dissolved in 25 ml of water and 25 ml of 95% EtOH, was cooled to 20 to 25° C. 2.9 g (50 mmol) of acetone and 10.6 g (100 mmol) of benzaldehyde were added, and a yellow precipitate formed. After 20 minutes the solution was filtered, and the solid was recrystallized from ethanol to afford the pure product as bright yellow flakes. The p.m.r. ($CHCl_3$, TMS) shows peaks at ppm 7.10 (d, 2H), 7.41–7.44 (m, 6H), 7.61–7.65 (m, 4H), and 7.75 (d, 2H).

Biological Activity

Figure 13:
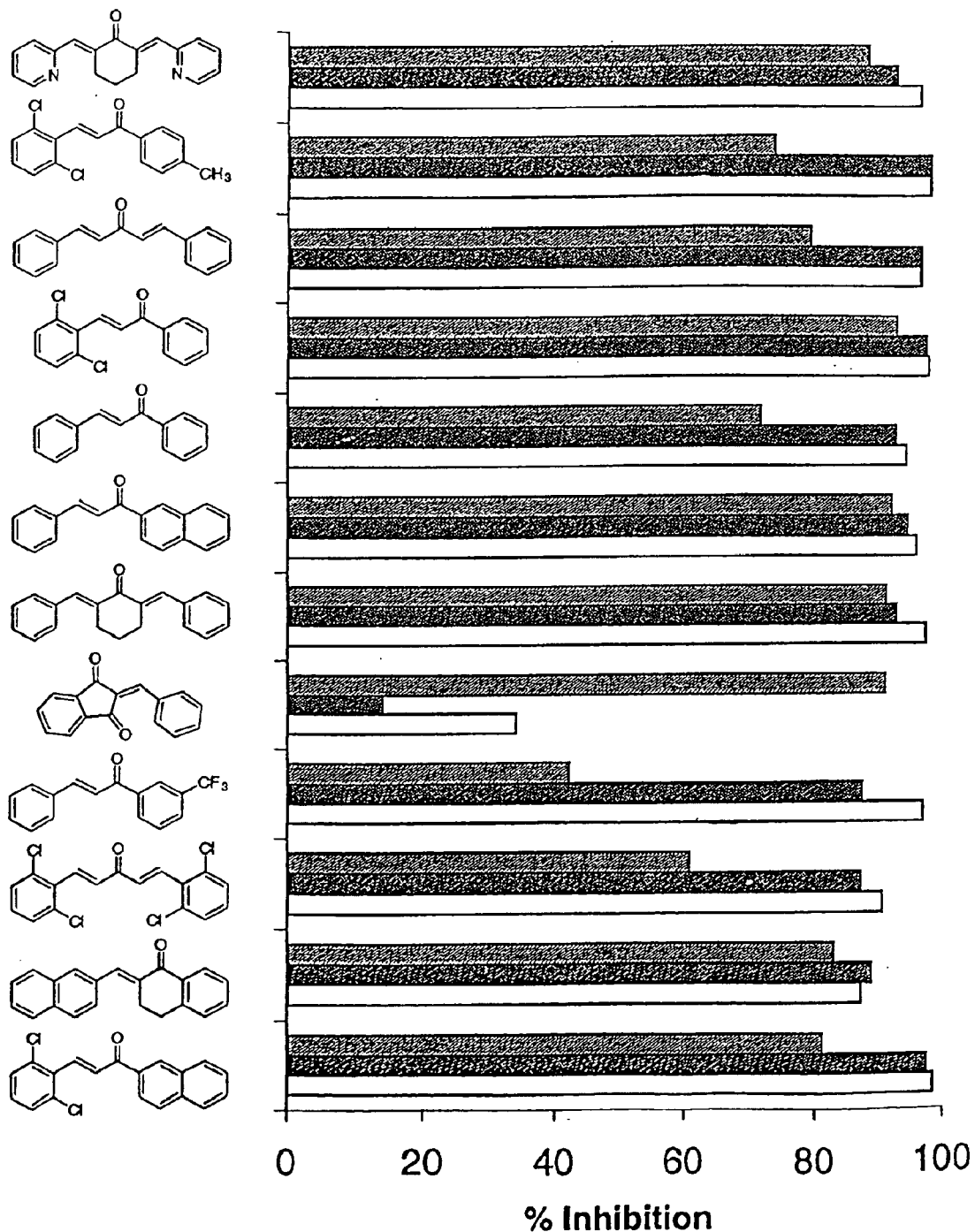
FIGS. 13–14 are diagrammatic representations in graph form of the biological activity of each of the indicated compounds at 1,3 and 6 µg/ml or 3, 6 and 9 µg/ml in inhibiting SVR cells according to the method of Arbiser, et al., *J. Am. Acad. Derm.*, pp. 925–929 (June, 1999).
Figure 14:
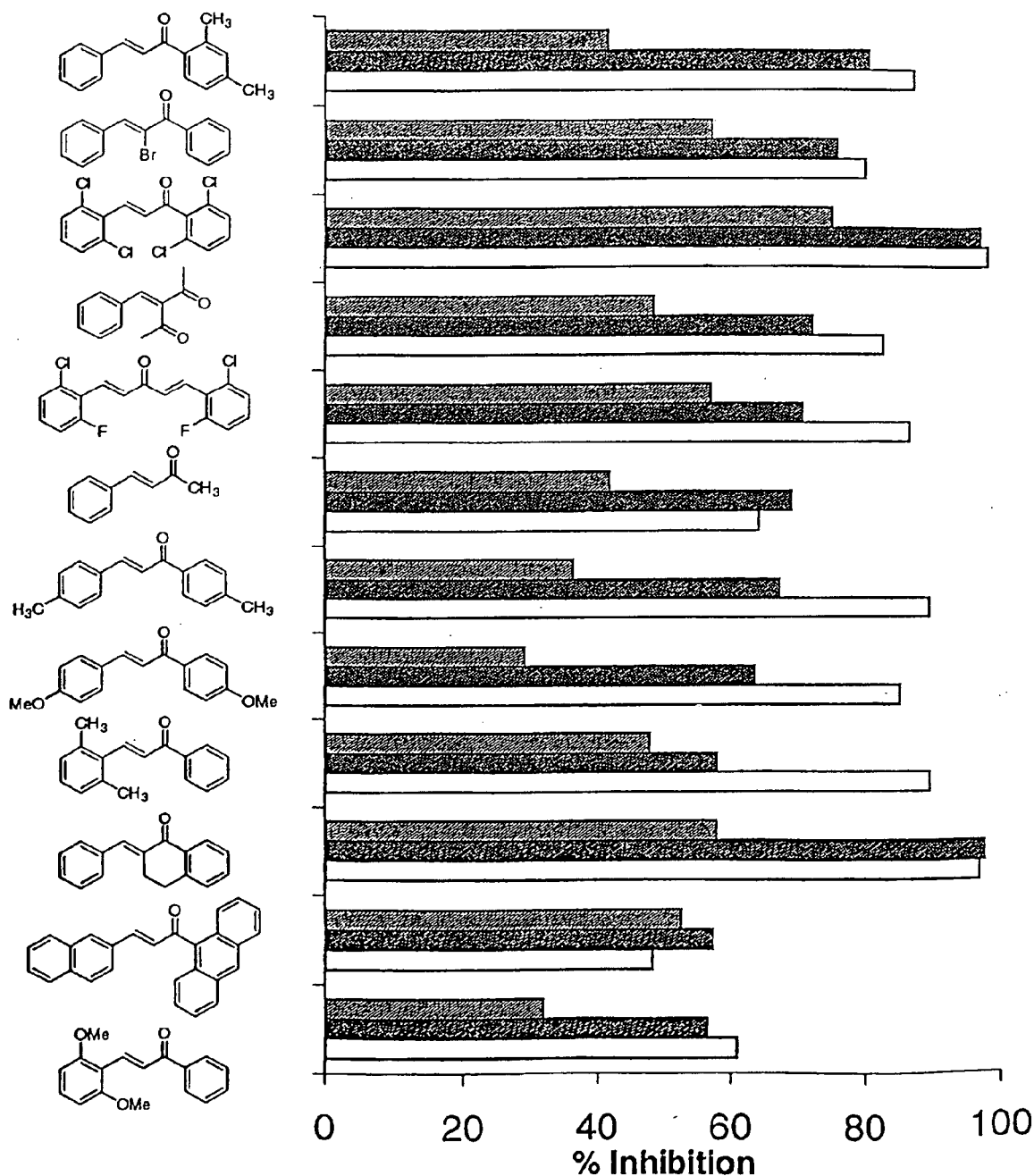

Biological Activity—Anti-Cancer Activity of Compounds According to the Present Invention 10,000 SVR cells were seeded in a 24 well dish [Arbiser, et al., *J. Am. Acad. Derm.*, pp. 925–929 (June, 1999)] and treated with various compounds (or control) according to the present invention at concentrations of 6 μg/ml, 3 μg/ml and 1 μg/ml, respectively, or 9 μg/ml, 6 μg/ml or 3 μg/ml, respectively (see Tables 1–6). The cell numbers were counted at 48 hours. The following tables 1–6 sets forth the results of the biological testing described above (see also FIGS. 13–14 for results). The results evidence that the present compounds as a class, evidence significant biological activity consistent with their use as anti-angiogenesis agents and in particular, anti-cancer agents according to the present invention.

TABLE 1

Biological Testing of Various Compound Classes

| Compounds | Percent Inhibition at a Specified Density (ug/ml) | | |
|---|---|---|---|
| | 1 | 3 | 6 |
| Chalcone (1) | 71.6 | 92.8 | 94.4 |
| 4,4'-Dimethoxychalcone (2) | 29.1 | 63.4 | 85.2 |
| 1,5-Diphenyl-1E,4E-pentadien-3-one (3) | 79.3 | 96.8 | 96.8 |
| 2,5-(Dibenzylidene)cyclopentanone (4) | 19.6 | 23.8 | 38.6 |
| 4-Phenyl-3E-buten-2-one (5) | 41.9 | 69.0 | 64.0 |
| 2-(Benzylidene)malononitrile (6) | 19.4 | 15.9 | 23.7 |
| 2-(Benzylidene)cyclohexanone (7) | 23.0 | 29.5 | 72.4 |
| 2-(Benzylidene)-1,3-indanedione (8) | 91.1 | 14.0 | 34.0 |
| 3-Benzylidene-2,4-pentanedione (9) | 48.3 | 72.0 | 82.7 |

TABLE 1-continued

Biological Testing of Various Compound Classes

| Compounds | Percent Inhibition at a Specified Density (ug/ml) | | |
|---|---|---|---|
| | 1 | 3 | 6 |
| trans-Cinnamic Acid (10) | 18.6 | 14.1 | 69.6 |
| para-Bromocinnamic Acid (11) | 18.2 | 3.5 | 0.0 |
| 3-Acetyl-6-bromocoumarin (12) | 20.0 | 12.7 | 17.4 |
| 3-Acetylcoumarin (13) | 26.0 | 4.9 | 13.0 |
| Flavone (14) | 19.3 | 26.3 | 46.7 |
| Chromone (15) | 20.6 | 8.2 | 20.8 |
| 6,8-Dichloro-3-cyanochromone (16) | 15.2 | 0.0 | 0.0 |

TABLE 2

Biological Testing of Purchased Chalcone Derivatives

| Compound | Percent Inhibition at a Specified Density (ug/ml) | | |
|---|---|---|---|
| | 1 | 3 | 6 |
| 4'-Carboxymethylchalcone (17) | 13.7 | 3.8 | 29.7 |
| 3'-(Trifluoromethyl)chalcone (18) | 42.2 | 87.4 | 96.9 |
| 4,4'-Dichlorochalcone (19) | 13.8 | 11.7 | 31.1 |
| 4,4'-Dimethylchalcone (20) | 36.6 | 67.3 | 89.5 |
| 2-Chloro-2',4'-dimethylchalcone (21) | 29.6 | 25.2 | 73.4 |
| 2',4'-Dimethylchalcone (22) | 41.7 | 80.4 | 87.2 |
| 2,6-Dimethyichalcone (23) | 47.7 | 57.9 | 89.6 |
| 4-Benzyloxy-4'-methylchalcone (24) | 18.4 | 5.1 | 17.0 |
| 4-Benzyloxy-4'-chlorochalcone (25) | 25.6 | 4.4 | 62.9 |
| 4-Isopropyl-4-methylchalcone (26) | 19.5 | 14.2 | 59.2 |
| 2,4-Dichloro-4'-methylchalcone (27) | 19.9 | 10.4 | 84.6 |
| 2,6-Dichloro-4'-methylchalcone (28) | 73.7 | 98.2 | 98.1 |
| 4'-Chloro-4-methylchalcone (29) | 29.9 | 40.2 | 58.5 |
| 4-Chloro-4'-methylchalcone (30) | 22.3 | 24.5 | 46.5 |

TABLE 3

Biological Testing of Synthesized Chalcone Derivatives

| Compound | Percent Inhibition at a Specified Density (ug/ml) | | | |
|---|---|---|---|---|
| | 1 | 3 | 6 | 9 |
| 2,6-Dichlorochalcone (31) | — | 92.9 | 97.5 | 97.9 |
| 2,2',6,6'-Tetrachlorochalcone (32) | — | 74.9 | 97.0 | 98.1 |
| 2',6'-Dichlorochalcone (33) | 2.23 | 51.1 | 88.7 | — |
| 2,2',3,3',4,4',5,5',6,6'-Decafluorochalcone (34) | 31.1 | 88.6 | 88.6 | — |
| 2,3,4,5,6-Pentafluorochalcone (35) | 0 | 0 | 0 | — |
| 2',3',4',5',6'-Pentafluorochalcone (36) | 6.6 | 55.6 | 88.7 | — |
| 2,2',6,6'-Tetramethoxychalcone (37) | 36.2 | 49.2 | 39.2 | — |
| 2',6'-Dimethoxychalcone (38) | 25.8 | 39.8 | 63.5 | — |
| 2,6-Dimethoxychalcone (39) | 31.8 | 56.4 | 60.8 | — |
| 2,6-Dichloro-2',6'-dimethoxychalcone (40) | 23.2 | 43.7 | 52.3 | — |
| α-Bromo-Z-chalcone (41) | 57.2 | 75.7 | 79.8 | — |
| 1,3-Diphenyl-1-propanone (42) | — | 16.3 | 49.4 | 75.8 |

TABLE 4

Biological Activity of Heterocyclic Derivatives of Chalcone

| Compound | Percent Inhibition at a Specific Density (ug/ml) | | | |
|---|---|---|---|---|
| | 1 | 3 | 6 | 9 |
| 1,3-Bis(2-furyl)propenone (43) | 7.7 | 8.1 | 12.0 | |
| 1-(2-Furyl)-3-phenylpropenone (44) | 28.2 | 57.7 | 90.2 | — |

TABLE 4-continued

Biological Activity of Heterocyclic Derivatives of Chalcone

| Compound | Percent Inhibition at a Specific Density (ug/ml) | | | |
|---|---|---|---|---|
| | 1 | 3 | 6 | 9 |
| 3-(2-Furyl)-1-phenylpropenone (45) | 9.8 | 1.0 | 0.0 | — |
| 1,3-Di(2-pyridyl)propenone (46) | 0.0 | 53.4 | 85.2 | — |
| 1-Phenyl-3-(2-pyridyl)propenone (47) | 40.7 | 89.1 | 96.9 | — |
| 1-Phenyl-3-(3-pyridyl)propenone (48) | 30.0 | 31.7 | 83.2 | — |
| 3-Phenyl-1-(2-pyrrolyl)propenone (49) | 8.3 | 11.4 | 19.4 | — |
| 1-Phenyl-3-(2-pyrrolyl)propenone (50) | 19.0 | 21.5 | 0.0 | — |

TABLE 5

Biological Activity of Polycyclic Derivatives of Chalcone

| Compound | Percent Inhibition at a Specific Density (ug/ml) | | | |
|---|---|---|---|---|
| | 1 | 3 | 6 | 9 |
| 1-(9-Anthryl)-3-phenylpropenone (51) | 25.5 | 46.4 | 69.0 | — |
| 3-(9-Anthryl)-1-phenylpropenone (52) | 54.6 | 53.5 | 71.3 | — |
| 1,3-Di(9-Anthryl)propenone (53) | 0.0 | 0.0 | 4.7 | — |
| 1-(9-Anthryl)-3-(2-naphthyl)propenone (54) | 52.5 | 57.3 | 48.1 | — |
| 1,3-Bis(4-biphenyl)propenone (55) | 19.2 | 0.0 | 0.0 | — |
| 1-(4-Biphenyl)-3-phenylpropenone (56) | 10.4 | 34.7 | 0.0 | — |
| 3-(4-Biphenyl)-1-phenylpropenone (57) | 24.9 | 12.9 | 41.4 | — |
| 1-(1-Naphthyl)-3-phenylpropenone (58) | 10.9 | 33.2 | 68.0 | — |
| 3-(2,6-Dichlorophenyl)-1-(2-naphthyl)propenone (59) | — | 81.0 | 97.4 | 98.3 |
| 1,3-Di(2-naphthyl)propenone (60) | — | 13.2 | 20.3 | 27.1 |
| 1-(2-Naphthyl)-3-phenylpropenone (61) | — | 92.2 | 94.7 | 96.0 |
| 3-(2-Naphthyl)-1-phenylpropenone (62) | — | 29.5 | 44.3 | 69.1 |
| 1-(2-Naphthyl)-3-(1-naphthyl)propenone (63) | 0.0 | 24.9 | 50.3 | — |
| 1-(1-Naphthyl)-3-(2-naphthyl)propenone (64) | 0.0 | 22.4 | 52.0 | — |
| 1,3-Di(1-naphthyl)propenone (65) | 12.0 | 55.5 | 60.3 | — |
| 3-Benzylidene-4-chromanone (66) | 12.3 | 23.8 | 54.3 | — |
| 3-(2,6-Dichlorobenzylidene)chromanone (67) | 5.4 | 3.6 | 12.5 | — |
| 2-(Benzylidene)tetralone (68) | — | 57.9 | 97.5 | 96.7 |
| 2-(2,6-Dichlorobenzylidene)tetralone (69) | 32.8 | 37.0 | 53.7 | — |
| 2-(1-Naphthylidene)tetralone (70) | 18.7 | 15.9 | 23.6 | — |
| 2-(2-Naphthylidene)tetralone (71) | — | 82.8 | 88.7 | 87.1 |

TABLE 6

Biological Activity of Cyclohexanone and Pentandienone Derivatives

| Compound Name | Percent Inhibition at Specific Density (ug/ml) | | | |
|---|---|---|---|---|
| | 1 | 3 | 6 | 9 |
| 1,5-Di(2-chloro-6-fluorophenyl)-1E,4E-pentadien-3-one (72) | 57.0 | 70.6 | 86.6 | — |
| 1,5-Bis(2,6-dichlorophenyl)-1E,4E-pentadien-3-one (73) | 60.7 | 87.1 | 90.4 | — |
| 1,5-Di(2-furyl)-1E,4E-pentadien-3-one (74) | 0.0 | 9.3 | 56.5 | — |
| 2,6-Di(benzylidene)cyclohexanone (75) | — | 91.3 | 92.8 | 97.4 |
| 2,6-Bis(2,6-dichlorobenzylidene)cyclohexanone (76) | 8.4 | 29.8 | 27.1 | — |
| 2,6-Di(1-naphthylidene)cyclohexanone (77) | 15.9 | 5.2 | 11.4 | — |
| 2,6-Di(2-naphthylidene)cyclohexanone (78) | 15.0 | 25.7 | 15.2 | — |
| 2,6-Di(2-pyridylidene)cyclohexanone (79) | 88.3 | 92.9 | 96.7 | — |

It is to be understood by those skilled in the art that the foregoing description and examples are illustrative of practicing the present invention, but are in no way limiting. Variations of the detail presented herein may be made without departing from the spirit and scope of the present invention as defined by the following claims.

What is claimed is:

1. A method of treating a tumor or cancer in a patient in need thereof comprising administering to said patient an effective amount of a compound according to the stmcture:

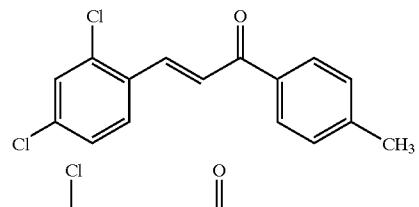

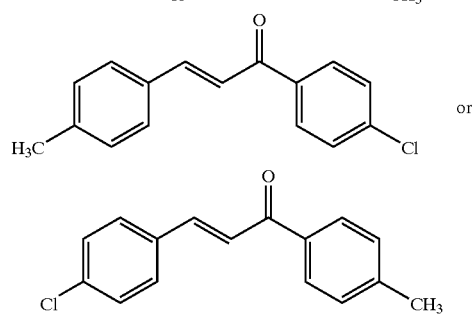

or

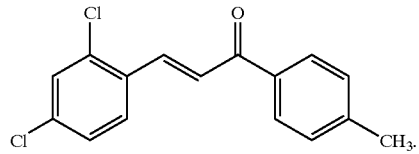

optionally in combination with a pharmaceutically acceptable excipient, additive or carrier.

2. The method according to claim 1 wherein said compound is

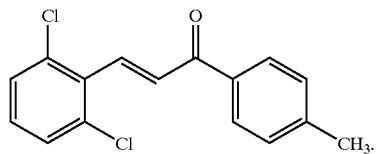

3. The method according to claim 1 wherein said compound is

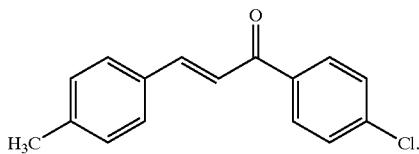

4. The method according to claim 1 wherein said compound is

5. The method according to claim 1 wherein said compound is

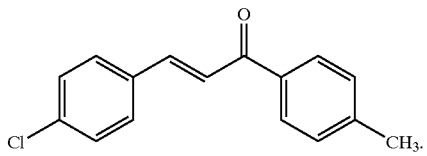

6. The method according to claim 1 wherein said tumor or cancer is selected from the group consisting of cervical, anal and oral cancers, eye or ocular cancer, stomach, colon, bladder, rectal, liver, pancreatic, lung, breast, cervix uteri, corpus uteri, ovary, prostate, testis, renal, brain/cns, head and neck, throat, skin melanoma, acute lymphocytic leukemia, acute myelogenous leukemia, Ewing's Sarcoma, Kaposi's Sarcoma, basal cell carinoma and squamous cell carcinoma, small cell lung cancer, choriocarcinoma, rhabdomyosarcoma, angiosarcoma, hemangioendothelioma, Wilms Tumor, neuroblastoma, mouth/pharynx, esophageal, larynx, kidney and lymphoma.

7. The method according to claim 2 wherein said tumor or cancer is selected from the group consisting of cervical, anal and oral cancers, eye or ocular cancer, stomach, colon, bladder, rectal, liver, pancreatic, lung, breast, cervix uteri, corpus uteri, ovary, prostate, testis, renal, brain/cns, head and neck, throat, skin melanoma, acute lymphocytic leukemia, acute myelogenous leukemia, Ewing's Sarcoma, Kaposi's Sarcoma, basal cell carinoma and squamous cell carcinoma, small cell lung cancer, choriocarcinoma, rhabdomyosarcoma, angiosarcoma, hemangioendothelioma, Wilms Tumor, neuroblastoma, mouth/pharynx, esophageal, larynx, kidney and lymphoma.

8. The method according to claim 3 wherein said tumor or cancer is selected from the group consisting of cervical, anal and oral cancers, eye or ocular cancer, stomach, colon, bladder, rectal, liver, pancreatic, lung, breast, cervix uteri, corpus uteri, ovary, prostate, testis, renal, brain/cns, head and neck, throat, skin melanoma, acute lymphocytic leukemia, acute myelogenous leukemia, Ewing's Sarcoma, Kaposi's Sarcoma, basal cell carinoma and squamous cell carcinoma, small cell lung cancer, choriocarcinoma, rhabdomyosarcoma, angiosarcoma, hemangioendothelioma, Wilms Tumor, neuroblastoma, mouth/pharynx, esophageal, larynx, kidney and lymphoma.

9. The method according to claim 4 wherein said tumor is selected from the group consisting of cervical, anal and oral cancers, eye or ocular cancer, stomach, colon, bladder, rectal, liver, pancreatic, lung, breast, cervix uteri, corpus uteri, ovary, prostate, testis, renal, brain/cns, head and neck, throat, skin melanoma, acute lymphocytic leukemia, acute myelogenous leukemia, Ewing's Sarcoma, Kaposi's Sarcoma, basal cell carinoma and squamous cell carcinoma, small cell lung cancer, choriocarcinoma, rhabdomyosarcoma, angiosarcoma, hemangioendothelioma, Wilms Tumor, neuroblastoma, mouth/pharynx, esophageal, larynx, kidney and lymphoma.

10. The method according to claim 5 wherein said tumor is selected from the group consisting of cervical, anal and oral cancers, eye or ocular cancer, stomach, colon, bladder, rectal, liver, pancreatic, lung, breast, cervix uteri, corpus uteri, ovary, prostate, testis, renal, brain/cns, head and neck, throat, skin melanoma, acute lymphocytic leukemia, acute myelogenous leukemia, Ewing's Sarcoma, Kaposi's Sarcoma, basal cell carinoma and squamous cell carcinoma, small cell lung cancer, choriocarcinoma, rhabdomyosarcoma, angiosarcoma, hemangioendothelioma, Wilms Tumor, neuroblastoma, mouth/pharynx, esophageal, larynx, kidney and lymphoma.

* * * * *